US007109027B2

(12) United States Patent
Peraus

(10) Patent No.: US 7,109,027 B2
(45) Date of Patent: Sep. 19, 2006

(54) Aβ-PEPTIDE SCREENING ASSAY

(75) Inventor: Gisela Peraus, München (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/794,975

(22) Filed: Feb. 27, 2001

(65) Prior Publication Data

US 2001/0034884 A1 Oct. 25, 2001

Related U.S. Application Data

(63) Continuation of application No. 09/455,367, filed on Dec. 3, 1999, now abandoned.

(30) Foreign Application Priority Data

Dec. 7, 1998 (DE) ................................ 198 56 261

(51) Int. Cl.
*C12N 15/85* (2006.01)

(52) U.S. Cl. ............................ 435/325; 435/4; 435/23; 435/29; 435/183; 435/254.11; 435/455

(58) Field of Classification Search .................... 435/4, 435/23, 29, 183, 254.11, 325, 455, 320.1, 435/6, 7.1, 7.2

See application file for complete search history.

(56) References Cited

U.S. PATENT DOCUMENTS 5,656,477 A * 8/1997 Vitek et al. ................. 435/325
5,667,992 A 9/1997 Casey et al.
5,744,346 A * 4/1998 Chrysler et al. ............ 435/226

FOREIGN PATENT DOCUMENTS

| | | |
|---|---|---|
| DE | 198 49 073 | 4/2000 |
| EP | 0 653 154 | 5/1995 |
| EP | 0 801 307 | 10/1997 |
| WO | WO 94/28412 | 12/1994 |
| WO | WO 96/40885 | 12/1996 |
| WO | WO 98/07850 | 2/1998 |
| WO | WO 98/15828 | 4/1998 |
| WO | WO 98/26059 | 6/1998 |

OTHER PUBLICATIONS

Ausubel et al, 1995, Short Protocols in Molecular Biology, Wiley Press, chapter 13, pp. 53-61.*
Bunnell et al, 1998, J. Biol. Chem., 273: 31947-31955.*
Evin et al, 1995, Biochemistry, 34: 14185-14192.*
Le Brocque et al, 1998, Biochemistry, 37, 14958-14965.*
Sadowski et al, 1988, Nature, 335, pp. 563-564.*
Tischer et al. (Journal of Biological Chemistry, 1996; vol. 271(36), pp. 21914-21919).*
German Patent Application No. 19849073.9 filed Oct. 24, 1998.
Cherest et al., The *Saccharomyces cerevisiae* MET3 gene: Nucleotide sequence and relationship of the 5' non-coding region to that of MET25, Mol. Gen. Genet., vol. 210, pp. 307-313, 1987.
Estus et al., "Potentially Amyloidogenic, Carboxyl-Terminal Derivatives of the Amyloid Protein Precursor", Science, vol. 255, pp. 726-728.
Haass et al., "Amyloid β-peptide is produced by cultured cells during normal metabolism", Nature, vol. 359, pp. 322-325, Sep. 24, 1992.
Hilbich et al., "Aggregation and Secondary Structure of Synthetic Amyloid βA4 Peptides of Alzheimer's Disease", J. Mol. Biol., vol. 218, pp. 149-163, 1991.
Kang et al., "The precursor of Alzheimer's disease amyloid A4 protein resembles a cell-surface receptor", Nature, vol. 325, pp. 733-736, Feb. 19, 1987.
Maruyama et al., "Cleave at the N-Terminal Site of Alzheimer Amyloid β/A4 Protein is Essential for its Secretion", Biochem. Biophy. Res. Commun., vol. 202, No. 3, pp. 1517-1523, Aug. 15, 1994.
Mumberg et al., "Regulatable promoters of Saccharomyces cerevisiae: comparison of transcriptional activity and their use for heterologous expression", Nucleic Acids Research, vol. 22, No. 5, pp. 5767-5768, 1994.
Punt et al., "A mini-promoter *lacZ* gene fusion for the analysis of fungal transcription control sequences", Gene, vol. 158, 119-123, 1995.
Rumble et al., "Amyloid A4 Protein and its Precursor in Down's Syndrome and Alzheimer's Disease", The New England Journal of Medicine, vol. 320, pp. 1446-1452, Jun. 1, 1989.
Sadowski et al., "GAL4-VP16 is an unusually potent transcriptional activator", Nature, vol. 335, pp. 563-564, Oct. 1998.

(Continued)

*Primary Examiner*—Anne-Marie Falk
*Assistant Examiner*—Jon Eric Angell
(74) *Attorney, Agent, or Firm*—Frommer Lawrence & Haug LLP

(57) ABSTRACT

The invention relates to a process for the determination of the γ-secretase activity, individual components of the process and the use of the process.

Figure 1:
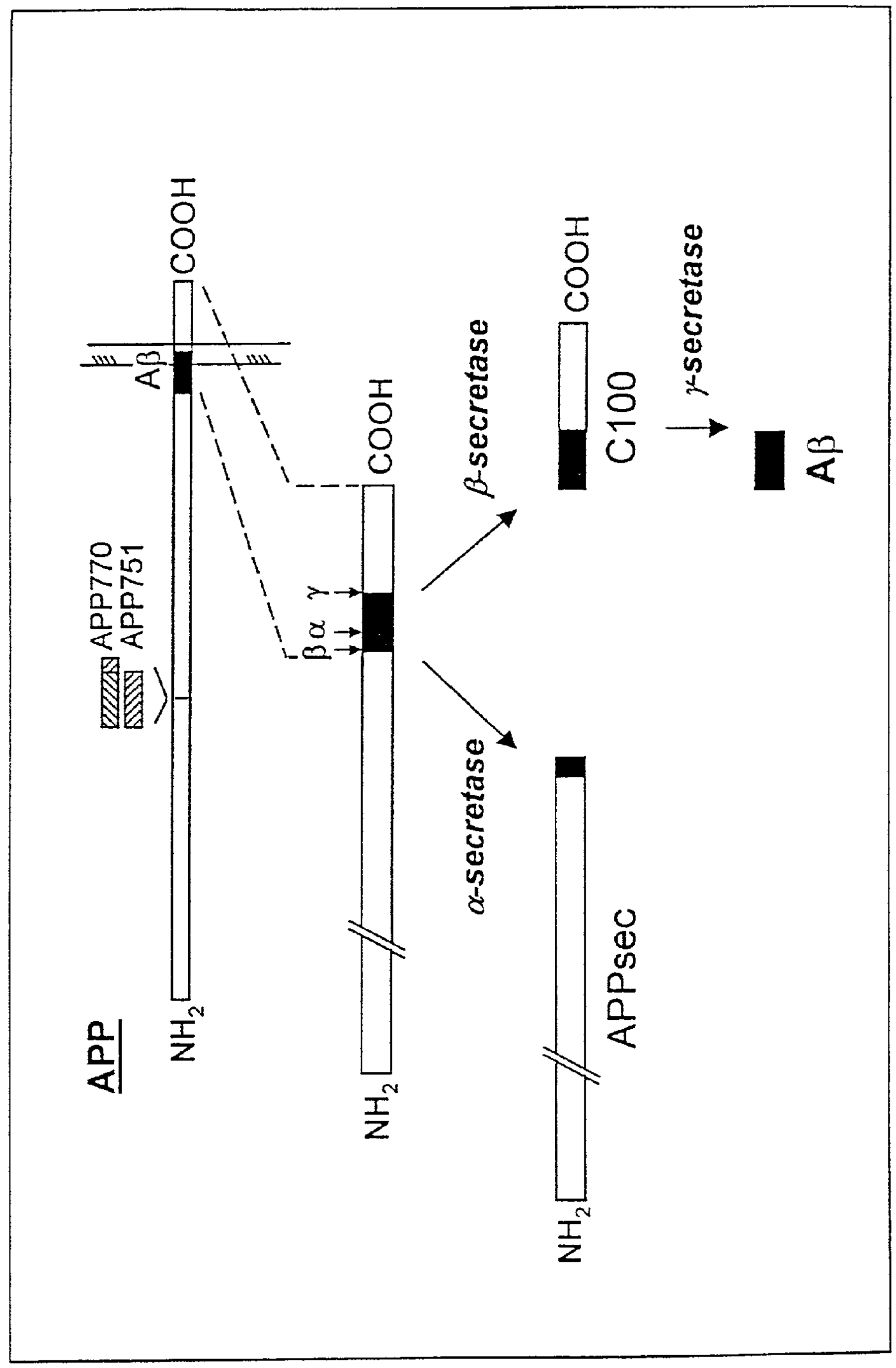

The present invention relates to a novel process for the determination of the γ-secretase activity and for the detection of γ-secretase; particular embodiments of the process relate on the one hand to processes for the identification of a γ-secretase or of a cDNA which codes for a γ-secretase and on the other hand to processes for the identification of substances which can inhibit the activity of a γ-secretase. Such substances have particular importance, as they can be used, for example, as pharmaceutical active compounds, e.g. for the treatment of Alzheimer's disease.

39 Claims, 4 Drawing Sheets

OTHER PUBLICATIONS

Scheuner et al., "Secreted amyloid β-protein similar to that in the senile plaques of Alzheimer's disease is increased *in vivo* by the presenilin 1 and 2 and APP mutations linked to familial Alzheimer's disease", Nature Medicine, vol. 2, No. 8, pp. 864-870, Aug. 1996.

Selleck et al., "Photofootprinting *in vivo detects* transcription-dependent changes in yeast TATA boxes", Nature, vol. 325, pp. 173-177, Jan. 1987.

Simons et al., "Amyloidogenic Processing of the Human Amyloid Precursor Protein in Primary Cultures of Rat Hippocampal Neurons", The Journal of Neuroscience, vol. 1, No. 16, pp. 899-908, Feb. 1, 1996.

Suzuki et al., "An Increased Percentage of Long Amyloid β Protein Secreted by Familial Amyloid β Protein Precursor (β $APP_{717}$) Mutants", Science, vol. 264, pp. 13361340, May 27, 1994.

Tartaglia et al., "A Novel Domain within the 55 TNF Receptor Signals Cell Death", Cell, vol. 74, pp. 845-853, Sep. 10, 1993.

Vickova et al., "The *Escherichia coli recA* gene increases UV-induced mitotic gene conversion in *Saccharomyces cerevisiae*", Curr. Genet, vol. 25, pp. 472-474, 1994.

Yankner et al., "Nerve Growth factor potentiates the neurotoxicity of β amyloid", Proc. Natl. Acad. Sci. USA, vol. 87, pp. 9020-9023, Nov. 1990.

Abstract: Link, C.D., "Transgenic *Caenorhabditis Elegans* as Model System to Study Amyloid Formation and Toxicity", Neurobiology Of Aging, US, Tarrytown, NY, Jul. 29, 1994; also referred to as XP002065640.

Wolfe, M.S., et al., "A Substrate-based Diflouro Ketone Selectivity Inhibits Alzheimer's Gamma-Secretase Activity", Journal Of Medicinal Chemistry, 1998: (41), pp. 6-9; also referred to as XP000938942.

Urmoneit, B., et al, "Cationic Lipids (Lipofectamine) and Disturbance of Cellular Cholesterol and Sphingomyelin Distribution Modulates Gamma-Secretase Activity Within Amyloid Precursor Protein *In Vitro*", Prostaglandinds And Other Lipid Mediators, 1998: (55), pp. 331-343, also referred to as XP004128238.

Cubitt, A. B. et al, "Understanding, Improving and Using Green Fluorescent Proteins", TIBS Trends In Biochemical Sciences, Nov. 1, 1995, pp. 448-455; also referred to as XP000606919.

Higaki et al, "Processing of Beta-Amyloid Precursor Protein by Cathepsin D", The Journal Of Biological Chemistry, 1996: (271), pp. 31885-31893; also referred to as XP002147307.

Lichtenhaler, S. F. et al, "A Novel Substrate for Analyzing Alzheimer's Disease Gamma-Secretase", FEBS Letters, 1999: (453), pp. 288-292; also referred to as XP 000937693.

Li, et al, "Intracellular Accumulation of Detergent-Soluble Amyloidogenic Aβ Fragment of Alzheimer's Disease Precursor Protein in the Hippocampus of Aged Transgenic Mice", Journal Of Neurochemistry, 1999: (72), pp. 2479-2487, also referred to as XP000912279.

* cited by examiner

SEQUENCE LISTING

```
<160> NUMBER OF SEQ ID NOS: 13

<210> SEQ ID NO 1
<211> LENGTH: 24
<212> TYPE: PRT
<213> ORGANISM: Homo sapiens

<400> SEQUENCE: 1

Gly Ala Ile Ile Gly Leu Met Val Gly Gly Val Val Ile Ala Thr Val
  1               5                  10                  15

Ile Val Ile Thr Leu Val Met Leu
             20


<210> SEQ ID NO 2
<211> LENGTH: 12
```

-continued

```
<212> TYPE: PRT
<213> ORGANISM: Homo sapiens

<400> SEQUENCE: 2

Gly Ala Ile Ile Gly Leu Met Val Gly Gly Val Val
  1               5                  10


<210> SEQ ID NO 3
<211> LENGTH: 9
<212> TYPE: PRT
<213> ORGANISM: Homo sapiens

<400> SEQUENCE: 3

Val Ile Val Ile Thr Leu Val Met Leu
  1               5


<210> SEQ ID NO 4
<211> LENGTH: 100
<212> TYPE: PRT
<213> ORGANISM: Homo sapiens

<400> SEQUENCE: 4

Leu Asp Ala Glu Phe Arg His Asp Ser Gly Tyr Glu Val His His Gln
  1               5                  10                  15

Lys Leu Val Phe Phe Ala Glu Asp Val Gly Ser Asn Lys Gly Ala Ile
             20                  25                  30

Ile Gly Leu Met Val Gly Gly Val Val Ile Ala Thr Val Ile Val Ile
         35                  40                  45

Thr Leu Val Met Leu Lys Lys Lys Gln Tyr Thr Ser Ile His His Gly
     50                  55                  60

Val Val Glu Val Asp Ala Ala Val Thr Pro Glu Glu Arg His Leu Ser
 65                  70                  75                  80

Lys Met Gln Gln Asn Gly Tyr Glu Asn Pro Thr Tyr Lys Phe Phe Glu
                 85                  90                  95

Gln Met Gln Asn
            100


<210> SEQ ID NO 5
<211> LENGTH: 17
<212> TYPE: PRT
<213> ORGANISM: Homo sapiens

<400> SEQUENCE: 5

Met Leu Pro Gly Leu Ala Leu Phe Leu Leu Ala Ala Trp Thr Ala Arg
  1               5                  10                  15

Ala


<210> SEQ ID NO 6
<211> LENGTH: 117
<212> TYPE: PRT
<213> ORGANISM: Homo sapiens

<400> SEQUENCE: 6

Met Leu Pro Gly Leu Ala Leu Phe Leu Leu Ala Ala Trp Thr Ala Arg
  1               5                  10                  15

Ala Leu Asp Ala Glu Phe Arg His Asp Ser Gly Tyr Glu Val His His
             20                  25                  30

Gln Lys Leu Val Phe Phe Ala Glu Asp Val Gly Ser Asn Lys Gly Ala
         35                  40                  45

Ile Ile Gly Leu Met Val Gly Gly Val Val Ile Ala Thr Val Ile Val
```

-continued

```
     50                  55                  60

Ile Thr Leu Val Met Leu Lys Lys Lys Gln Tyr Thr Ser Ile His His
 65                  70                  75                  80

Gly Val Val Glu Val Asp Ala Ala Val Thr Pro Glu Glu Arg His Leu
                 85                  90                  95

Ser Lys Met Gln Gln Asn Gly Tyr Glu Asn Pro Thr Tyr Lys Phe Phe
            100                 105                 110

Glu Gln Met Gln Asn
        115


<210> SEQ ID NO 7
<211> LENGTH: 232
<212> TYPE: PRT
<213> ORGANISM: Artificial Sequence
<220> FEATURE:
<223> OTHER INFORMATION: Description of Artificial Sequence: mutagen

<400> SEQUENCE: 7

Met Lys Leu Leu Ser Ser Ile Glu Gln Ala Cys Asp Ile Cys Arg Leu
  1               5                  10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
     50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Trp Ala Pro Pro Thr Asp Val
145                 150                 155                 160

Ser Leu Gly Asp Glu Leu His Leu Asp Gly Glu Asp Val Ala Met Ala
                165                 170                 175

His Ala Asp Ala Leu Asp Asp Phe Asp Leu Asp Met Leu Gly Asp Gly
            180                 185                 190

Asp Ser Pro Gly Pro Gly Phe Thr Pro His Asp Ser Ala Pro Tyr Gly
        195                 200                 205

Ala Leu Asp Met Ala Asp Phe Glu Phe Glu Gln Met Phe Thr Asp Ala
    210                 215                 220

Leu Gly Ile Asp Glu Tyr Gly Gly
225                 230


<210> SEQ ID NO 8
<211> LENGTH: 1813
<212> TYPE: DNA
<213> ORGANISM: Artificial Sequence
<220> FEATURE:
<223> OTHER INFORMATION: Description of Artificial Sequence: mutagen

<400> SEQUENCE: 8
```

-continued

```
ggcaaggctt gaccgacaat tgcatgaaga atctgcttag ggttaggcgt tttgcgctgc     60

ttcgcgatgt acgggccaga tatacgcgtt gacattgatt attgactagt tattaatagt    120

aatcaattac ggggtcatta gttcatagcc catatatgga gttccgcgtt acataactta    180

cggtaaatgg cccgcctggc tgaccgccca acgacccccg cccattgacg tcaataatga    240

cgtatgttcc catagtaacg ccaataggga ctttccattg acgtcaatgg gtggactatt    300

tacggtaaac tgcccacttg gcagtacatc aagtgtatca tatgccaagt acgcccccta    360

ttgacgtcaa tgacggtaaa tggcccgcct ggcattatgc ccagtacatg accttatggg    420

actttcctac ttggcagtac atctacgtat tagtcatcgc tattaccatg gtgatgcggt    480

tttggcagta catcaatggg cgtggatagc ggtttgactc acggggattt ccaagtctcc    540

accccattga cgtcaatggg agtttgtttt ggcaccgcgt gtacggtggg aggtctatat    600

aagcagagct ctctggctaa ctagagaacc cactgcttac tggcttatcg aaattaatac    660

gactcactat agggagaccc aagctggcta gcgtttaaac ttaagcttca cagctagcgc    720

actcggtgcc ccgcgcaggg tcgcgatgct gcccggtttg gcactgttcc tgctggccgc    780

ctggacggct cgggcgctgg atgcagaatt ccgacatgac tcaggatatg aagttcatca    840

tcaaaaattg gtgttctttg cagaagatgt gggttcaaac aaaggtgcaa tcattggact    900

catggtgggc ggtgttgtca tagcgacagt gatcgtcatc accttggtga tgctgaagaa    960

gaaacagtac acatccattc atcatggtgt ggtggaggtt gacgccgctg tcaccccaga   1020

ggagcgccac ctgtccaaga tgcagcagaa cggctacgaa aatccaacct acaagttctt   1080

tgagcagatg cagaacgcgc ggggtacccc ggcgatgaag ctactgtctt ctatcgaaca   1140

agcatgcgat atttgccgac ttaaaaagct caagtgctcc aaagaaaaac cgaagtgcgc   1200

caagtgtctg aagaacaact gggagtgtcg ctactctccc aaaaccaaaa ggtctccgct   1260

gactagggca catctgacag aagtggaatc aaggctagaa agactggaac agctatttct   1320

actgattttt cctcgagaag accttgacat gattttgaaa atggattctt tacaggatat   1380

aaaagcattg ttaacaggat tatttgtaca agataatgtg aataaagatg ccgtcacaga   1440

tagattggct tcagtggaga ctgatatgcc tctaacattg agacagcata gaataagtgc   1500

gacatcatca tcggaagaga gtagtaacaa aggtcaaaga cagttgactg tatcgccgga   1560

attcccgggg atctgggccc ccccgaccga tgtcagcctg ggggacgagc tccacttaga   1620

cggcgaggac gtggcgatgg cgcatgccga cgcgctagac gatttcgatc tggacatgtt   1680

gggggacggg gattccccgg gccgggattt taccccccac gactccgccc cctacggcgc   1740

tctggatatg gccgacttcg agtttgagca gatgtttacc gatgcccttg gaattgacga   1800

gtacggtggg tag                                                      1813
```

<210> SEQ ID NO 9
<211> LENGTH: 5432
<212> TYPE: DNA
<213> ORGANISM: Artificial Sequence
<220> FEATURE:
<223> OTHER INFORMATION: Description of Artificial Sequence: mutagen

<400> SEQUENCE: 9

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240
```

-continued gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttggta ccgagctcgg atccactagt ccagtgtggt ggaattctgc 960
agatatccag cacagtggcg gccgctcgag tctagagggc ccgtttaaac ccgctgatca 1020
gcctcgactg tgccttctag ttgccagcca tctgttgttt gcccctcccc cgtgccttcc 1080
ttgaccctgg aaggtgccac tcccactgtc ctttcctaat aaaatgagga aattgcatcg 1140
cattgtctga gtaggtgtca ttctattctg gggggtgggg tggggcagga cagcaagggg 1200
gaggattggg aagacaatag caggcatgct ggggatgcgg tgggctctat ggcttctgag 1260
gcggaaagaa ccagctgggg ctctaggggg tatccccacg cgccctgtag cggcgcatta 1320
agcgcggcgg gtgtggtggt tacgcgcagc gtgaccgcta cacttgccag cgccctagcg 1380
cccgctcctt tcgctttctt cccttccttt ctcgccacgt tcgccggctt tccccgtcaa 1440
gctctaaatc ggggcatccc tttagggttc cgatttagtg ctttacggca cctcgacccc 1500
aaaaaacttg attagggtga tggttcacgt agtgggccat cgccctgata gacggttttt 1560
cgccctttga cgttggagtc cacgttcttt aatagtggac tcttgttcca aactggaaca 1620
acactcaacc ctatctcggt ctattctttt gatttataag ggattttggg gatttcggcc 1680
tattggttaa aaaatgagct gatttaacaa aaatttaacg cgaattaatt ctgtggaatg 1740
tgtgtcagtt agggtgtgga aagtccccag gctccccagg caggcagaag tatgcaaagc 1800
atgcatctca attagtcagc aaccaggtgt ggaaagtccc caggctcccc agcaggcaga 1860
agtatgcaaa gcatgcatct caattagtca gcaaccatag tcccgcccct aactccgccc 1920
atcccgcccc taactccgcc cagttccgcc cattctccgc cccatggctg actaattttt 1980
tttatttatg cagaggccga ggccgcctct gcctctgagc tattccagaa gtagtgagga 2040
ggcttttttg gaggcctagg cttttgcaaa aagctcccgg gagcttgtat atccattttc 2100
ggatctgatc aagagacagg atgaggatcg tttcgcatga ttgaacaaga tggattgcac 2160
gcaggttctc cggccgcttg ggtggagagg ctattcggct atgactgggc acaacagaca 2220
atcggctgct ctgatgccgc cgtgttccgg ctgtcagcgc aggggcgccc ggttcttttt 2280
gtcaagaccg acctgtccgg tgccctgaat gaactgcagg acgaggcagc gcggctatcg 2340
tggctggcca cgacgggcgt tccttgcgca gctgtgctcg acgttgtcac tgaagcggga 2400
agggactggc tgctattggg cgaagtgccg gggcaggatc tcctgtcatc tcaccttgct 2460
cctgccgaga aagtatccat catggctgat gcaatgcggc ggctgcatac gcttgatccg 2520
gctacctgcc cattcgacca ccaagcgaaa catcgcatcg agcgagcacg tactcggatg 2580

-continued

```
gaagccggtc ttgtcgatca ggatgatctg gacgaagagc atcaggggct cgcgccagcc   2640
gaactgttcg ccaggctcaa ggcgcgcatg cccgacggcg aggatctcgt cgtgacccat   2700
ggcgatgcct gcttgccgaa tatcatggtg gaaaatggcc gcttttctgg attcatcgac   2760
tgtggccggc tgggtgtggc ggaccgctat caggacatag cgttggctac ccgtgatatt   2820
gctgaagagc ttggcggcga atgggctgac cgcttcctcg tgctttacgg tatcgccgct   2880
cccgattcgc agcgcatcgc cttctatcgc cttcttgacg agttcttctg agcgggactc   2940
tggggttcga aatgaccgac caagcgacgc ccaacctgcc atcacgagat ttcgattcca   3000
ccgccgcctt ctatgaaagg ttgggcttcg gaatcgtttt ccgggacgcc ggctggatga   3060
tcctccagcg cggggatctc atgctggagt tcttcgccca ccccaacttg tttattgcag   3120
cttataatgg ttacaaataa agcaatagca tcacaaattt cacaaataaa gcattttttt   3180
cactgcattc tagttgtggt ttgtccaaac tcatcaatgt atcttatcat gtctgtatac   3240
cgtcgacctc tagctagagc ttggcgtaat catggtcata gctgtttcct gtgtgaaatt   3300
gttatccgct cacaattcca cacaacatac gagccggaag cataaagtgt aaagcctggg   3360
gtgcctaatg agtgagctaa ctcacattaa ttgcgttgcg ctcactgccc gctttccagt   3420
cgggaaacct gtcgtgccag ctgcattaat gaatcggcca acgcgcgggg agaggcggtt   3480
tgcgtattgg gcgctcttcc gcttcctcgc tcactgactc gctgcgctcg gtcgttcggc   3540
tgcggcgagc ggtatcagct cactcaaagg cggtaatacg gttatccaca gaatcagggg   3600
ataacgcagg aaagaacatg tgagcaaaag gccagcaaaa ggccaggaac cgtaaaaagg   3660
ccgcgttgct ggcgtttttc cataggctcc gcccccctga cgagcatcac aaaaatcgac   3720
gctcaagtca gaggtggcga aacccgacag gactataaag ataccaggcg tttccccctg   3780
gaagctccct cgtgcgctct cctgttccga ccctgccgct taccggatac ctgtccgcct   3840
ttctcccttc gggaagcgtg gcgctttctc aatgctcacg ctgtaggtat ctcagttcgg   3900
tgtaggtcgt tcgctccaag ctgggctgtg tgcacgaacc ccccgttcag cccgaccgct   3960
gcgccttatc cggtaactat cgtcttgagt ccaacccggt aagacacgac ttatcgccac   4020
tggcagcagc cactggtaac aggattagca gagcgaggta tgtaggcggt gctacagagt   4080
tcttgaagtg gtggcctaac tacggctaca ctagaaggac agtatttggt atctgcgctc   4140
tgctgaagcc agttaccttc ggaaaaagag ttggtagctc ttgatccggc aaacaaacca   4200
ccgctggtag cggtggtttt tttgtttgca agcagcagat tacgcgcaga aaaaaaggat   4260
ctcaagaaga tcctttgatc ttttctacgg ggtctgacgc tcagtggaac gaaaactcac   4320
gttaagggat tttggtcatg agattatcaa aaaggatctt cacctagatc cttttaaatt   4380
aaaaatgaag ttttaaatca atctaaagta tatatgagta aacttggtct gacagttacc   4440
aatgcttaat cagtgaggca cctatctcag cgatctgtct atttcgttca tccatagttg   4500
cctgactccc cgtcgtgtag ataactacga tacgggaggg cttaccatct ggccccagtg   4560
ctgcaatgat accgcgagac ccacgctcac cggctccaga tttatcagca ataaaccagc   4620
cagccggaag ggccgagcgc agaagtggtc ctgcaacttt atccgcctcc atccagtcta   4680
ttaattgttg ccgggaagct agagtaagta gttcgccagt taatagtttg cgcaacgttg   4740
ttgccattgc tacaggcatc gtggtgtcac gctcgtcgtt tggtatggct tcattcagct   4800
ccggttccca acgatcaagg cgagttacat gatcccccat gttgtgcaaa aaagcggtta   4860
gctccttcgg tcctccgatc gttgtcagaa gtaagttggc cgcagtgtta tcactcatgg   4920
ttatggcagc actgcataat tctcttactg tcatgccatc cgtaagatgc ttttctgtga   4980
```

-continued

```
ctggtgagta ctcaaccaag tcattctgag aatagtgtat gcggcgaccg agttgctctt   5040

gcccggcgtc aatacgggat aataccgcgc cacatagcag aactttaaaa gtgctcatca   5100

ttggaaaacg ttcttcgggg cgaaaactct caaggatctt accgctgttg agatccagtt   5160

cgatgtaacc cactcgtgca cccaactgat cttcagcatc ttttactttc accagcgttt   5220

ctgggtgagc aaaaacagga aggcaaaatg ccgcaaaaaa gggaataagg gcgacacgga   5280

aatgttgaat actcatactc ttcctttttc aatattattg aagcatttat cagggttatt   5340

gtctcatgag cggatacata tttgaatgta tttagaaaaa taaacaaata ggggttccgc   5400

gcacatttcc ccgaaaagtg ccacctgacg tc                                 5432
```

<210> SEQ ID NO 10
<211> LENGTH: 3354
<212> TYPE: DNA
<213> ORGANISM: Homo sapiens

<400> SEQUENCE: 10

```
agtttcctcg gcagcggtag gcgagagcac gcggaggagc gtgcgcgggg gccccgggag     60

acggcggcgg tggcggcgcg ggcagagcaa ggacgcggcg gatcccactc gcacagcagc    120

gcactcggtg ccccgcgcag ggtcgcgatg ctgcccggtt tggcactgct cctgctggcc    180

gcctggacgg ctcgggcgct ggaggtaccc actgatggta atgctggcct gctggctgaa    240

ccccagattg ccatgttctg tggcagactg aacatgcaca tgaatgtcca gaatgggaag    300

tgggattcag atccatcagg gaccaaaacc tgcattgata ccaaggaagg catcctgcag    360

tattgccaag aagtctaccc tgaactgcag atcaccaatg tggtagaagc caaccaacca    420

gtgaccatcc agaactggtg caagcggggc cgcaagcagt gcaagaccca tccccacttt    480

gtgattccct accgctgctt agttggtgag tttgtaagtg atgcccttct cgttcctgac    540

aagtgcaaat tcttacacca ggagaggatg gatgtttgcg aaactcatct tcactggcac    600

accgtcgcca aagagacatg cagtgagaag agtaccaact tgcatgacta cggcatgttg    660

ctgccctgcg gaattgacaa gttccgaggg gtagagtttg tgtgttgccc actggctgaa    720

gaaagtgaca atgtggattc tgctgatgcg gaggaggatg actcggatgt ctggtggggc    780

ggagcagaca cagactatgc agatgggagt gaagacaaag tagtagaagt agcagaggag    840

gaagaagtgg ctgaggtgga agaagaagaa gccgatgatg acgaggacga tgaggatggt    900

gatgaggtag aggaagaggc tgaggaaccc tacgaagaag ccacagagag aaccaccagc    960

attgccacca ccaccaccac caccacagag tctgtggaag aggtggttcg agttcctaca   1020

acagcagcca gtacccctga tgccgttgac aagtatctcg agacacctgg ggatgagaat   1080

gaacatgccc atttccagaa agccaaagag aggcttgagg ccaagcaccg agagagaatg   1140

tcccaggtca tgagagaatg ggaagaggca gaacgtcaag caaagaactt gcctaaagct   1200

gataagaagg cagttatcca gcatttccag gagaaagtgg aatctttgga acaggaagca   1260

gccaacgaga gacagcagct ggtggagaca cacatggcca gagtggaagc catgctcaat   1320

gaccgccgcc gcctggccct ggagaactac atcaccgctc tgcaggctgt tcctcctcgg   1380

cctcgtcacg tgttcaatat gctaaagaag tatgtccgcg cagaacagaa ggacagacag   1440

cacaccctaa agcatttcga gcatgtgcgc atggtggatc ccaagaaagc cgctcagatc   1500

cggtcccagg ttatgacaca cctccgtgtg atttatgagc gcatgaatca gtctctctcc   1560

ctgctctaca acgtgcctgc agtggccgag gagattcagg atgaagttga tgagctgctt   1620
```

-continued

```
cagaaagagc aaaactattc agatgacgtc ttggccaaca tgattagtga accaaggatc   1680

agttacggaa acgatgctct catgccatct ttgaccgaaa cgaaaaccac cgtggagctc   1740

cttcccgtga atggagagtt cagcctggac gatctccagc cgtggcattc ttttggggct   1800

gactctgtgc cagccaacac agaaaacgaa gttgagcctg ttgatgcccg ccctgctgcc   1860

gaccgaggac tgaccactcg accaggttct gggttgacaa atatcaagac ggaggagatc   1920

tctgaagtga agatggatgc agaattccga catgactcag gatatgaagt tcatcatcaa   1980

aaattggtgt tctttgcaga agatgtgggt tcaaacaaag gtgcaatcat tggactcatg   2040

gtgggcggtg ttgtcatagc gacagtgatc gtcatcacct tggtgatgct gaagaagaaa   2100

cagtacacat ccattcatca tggtgtggtg gaggttgacg ccgctgtcac cccagaggag   2160

cgccacctgt ccaagatgca gcagaacggc tacgaaaatc caacctacaa gttctttgag   2220

cagatgcaga actagacccc cgccacagca gcctctgaag ttggacagca aaaccattgc   2280

ttcactaccc atcggtgtcc atttatagaa taatgtggga agaaacaaac ccgttttatg   2340

atttactcat tatcgccttt tgacagctgt gctgtaacac aagtagatgc ctgaacttga   2400

attaatccac acatcagtaa tgtattctat ctctctttac attttggtct ctatactaca   2460

ttattaatgg gttttgtgta ctgtaaagaa tttagctgta tcaaactagt gcatgaatag   2520

attctctcct gattatttat cacatagccc cttagccagt tgtatattat tcttgtggtt   2580

tgtgacccaa ttaagtccta ctttacatat gctttaagaa tcgatggggg atgcttcatg   2640

tgaacgtggg agttcagctg cttctcttgc ctaagtattc ctttcctgat cactatgcat   2700

tttaaagtta aacattttta agtatttcag atgctttaga gagatttttt ttccatgact   2760

gcattttact gtacagattg ctgcttctgc tatatttgtg atataggaat taagaggata   2820

cacacgtttg tttcttcgtg cctgttttat gtgcacacat taggcattga gacttcaagc   2880

ttttcttttt ttgtccacgt atctttgggt ctttgataaa gaaaagaatc cctgttcatt   2940

gtaagcactt ttacggggcg ggtggggagg ggtgctctgc tggtcttcaa ttaccaagaa   3000

ttctccaaaa caattttctg caggatgatt gtacagaatc attgcttatg acatgatcgc   3060

tttctacact gtattacata aataaattaa ataaaataac cccgggcaag acttttcttt   3120

gaaggatgac tacagacatt aaataatcga agtaattttg ggtggggaga agaggcagat   3180

tcaatttcct ttaaccagtc tgaagtttca tttatgatac aaaagaagat gaaaatggaa   3240

gtggcaatat aaggggatga ggaaggcatg cctggacaaa cccttctttt aagatgtgtc   3300

ttcaatttgt ataaaatggt gttttcatgt aaataaatac attcttggag gagc         3354
```

<210> SEQ ID NO 11
<211> LENGTH: 8667
<212> TYPE: DNA
<213> ORGANISM: Artificial Sequence
<220> FEATURE:
<223> OTHER INFORMATION: Description of Artificial Sequence: mutagen

<400> SEQUENCE: 11

```
gacgaaaggg cctcgtgata cgcctatttt tataggttaa tgtcatgata ataatggttt     60

cttaggacgg atcgcttgcc tgtaacttac acgcgcctcg tatcttttaa tgatggaata    120

atttgggaat ttactctgtg tttatttatt tttatgtttt gtatttggat tttagaaagt    180

aaataaagaa ggtagaagag ttacggaatg aagaaaaaaa aataaacaaa ggtttaaaaa    240

atttcaacaa aaagcgtact ttacatatat atttattaga caagaaaagc agattaaata    300

gatatacatt cgattaacga taagtaaaat gtaaaatcac aggattttcg tgtgtggtct    360
```

-continued

```
tctacacaga caagatgaaa caattcggca ttaatacctg agagcaggaa gagcaagata    420
aaaggtagta tttgttggcg atccccctag agtcttttac atcttcggaa aacaaaaact    480
atttttttctt taatttcttt ttttactttc tatttttaat ttatatattt atattaaaaa    540
atttaaatta taattatttt tatagcacgt gatgaaaagg acccaggtgg cacttttcgg    600
ggaaatgtgc gcggaacccc tatttgttta tttttctaaa tacattcaaa tatgtatccg    660
ctcatgagac aataaccctg ataaatgctt caataatctg cagctctggc ccgtgtctca    720
aaatctctga tgttacattg cacaagataa aaatatatca tcatgaacaa taaaactgtc    780
tgcttacata aacagtaata caaggggtgt tatgagccat attcaacggg aaacgtcttg    840
ctggaggccg cgattaaatt ccaacatgga tgctgattta tatgggtata aatgggctcg    900
cgataatgtc gggcaatcag gtgcgacaat ctttcgattg tatgggaagc ccgatgcgcc    960
agagttgttt ctgaaacatg gcaaaggtag cgttgccaat gatgttacag atgagatggt   1020
cagactaaac tggctgacgg aatttatgcc tcttccgacc atcaagcatt ttatccgtac   1080
tcctgatgat gcatggttac tcaccactgc gatccgcggg aaaacagcat tccaggtatt   1140
agaagaatat cctgattcag gtgaaaatat tgttgatgcg ctggcagtgt tcctgcgccg   1200
gttgcattcg attcctgttt gtaattgtcc ttttaacagc gatcgcgtat ttcgtctcgc   1260
tcaggcgcaa tcacgaatga ataacggttt ggttgatgcg agtgattttg atgacgagcg   1320
taatggctgg cctgttgaac aagtctggaa agaaatgcat acgcttttgc cattctcacc   1380
ggattcagtc gtcactcatg gtgatttctc acttgataac cttatttttg acgaggggaa   1440
attaataggt tgtattgatg ttggacgagt cggaatcgca gaccgatacc aggatcttgc   1500
catcctatgg aactgcctcg gtgagttttc tccttcatta cagaaacggc tttttcaaaa   1560
atatggtatt gataatcctg atatgaataa attgcagttt catttgatgc tcgatgagtt   1620
tttctaatca gaattggtta attggttgta acactggcag agcattacgc tgacttgacg   1680
ggacggcgca tgaccaaaat cccttaacgt gagttttcgt tccactgagc gtcagacccc   1740
gtagaaaaga tcaaaggatc ttcttgagat cctttttttc tgcgcgtaat ctgctgcttg   1800
caaacaaaaa aaccaccgct accagcggtg gtttgtttgc cggatcaaga gctaccaact   1860
ctttttccga aggtaactgg cttcagcaga gcgcagatac caaatactgt ccttctagtg   1920
tagccgtagt taggccacca cttcaagaac tctgtagcac cgcctacata cctcgctctg   1980
ctaatcctgt taccagtggc tgctgccagt ggcgataagt cgtgtcttac cgggttggac   2040
tcaagacgat agttaccgga taaggcgcag cggtcgggct gaacgggggg ttcgtgcaca   2100
cagcccagct tggagcgaac gacctacacc gaactgagat acctacagcg tgagcattga   2160
gaaagcgcca cgcttcccga agggagaaag gcggacaggt atccggtaag cggcagggtc   2220
ggaacaggag agcgcacgag ggagcttcca gggggaaacg cctggtatct ttatagtcct   2280
gtcgggtttc gccacctctg acttgagcgt cgatttttgt gatgctcgtc aggggggccg   2340
agcctatgga aaaacgccag caacgcggcc tttttacggt tcctggcctt ttgctggcct   2400
tttgctcaca tgttctttcc tgcgttatcc cctgattctg tggataaccg tattaccgcc   2460
tttgagtgag ctgataccgc tcgccgcagc cgaacgaccg agcgcagcga gtcagtgagc   2520
gaggaagcgg aagagcgccc aatacgcaaa ccgcctctcc ccgcgcgttg gccgattcat   2580
taatgcagct ggcacgacag gtttcccgac tggaaagcgg gcagtgagcg caacgcaatt   2640
aatgtgagtt acctcactca ttaggcaccc caggctttac actttatgct tccggctcct   2700
```

-continued

```
atgttgtgtg gaattgtgag cggataacaa tttcacacag gaaacagcta tgaccatgat   2760
tacgccaagc tcggaattaa ccctcactaa agggaacaaa agctggtacc gatcccgagc   2820
tttgcaaatt aaagccttcg agcgtcccaa aaccttctca agcaaggttt tcagtataat   2880
gttacatgcg tacacgcgtc tgtacagaaa aaaaagaaaa atttgaaata taaataacgt   2940
tcttaatact aacataacta taaaaaaata aatagggacc tagacttcag gttgtctaac   3000
tccttccttt tcggttagag cggatgtggg gggagggcgt gaatgtaagc gtgacataac   3060
taattacatg atatcgacaa aggaaaaggg gcctgtttac tcacaggctt ttttcaagta   3120
ggtaattaag tcgtttctgt ctttttcctt cttcaaccca ccaaaggcca tcttggtact   3180
tttttttttt tttttttttt tttttttttt tttttttttt tttttttttt tttttttttt   3240
tttttttttt tttttttttt tttttttttt tttcatagaa ataatacaga agtagatgtt   3300
gaattagatt aaactgaaga tatataattt attggaaaat acatagagct ttttgttgat   3360
gcgcttaagc gatcaattca acaacaccac cagcagctct gatttttttct tcagccaact   3420
tggagacgaa tctagctttg acgataactg gaacatttgg aattctaccc ttacccaaga   3480
tcttaccgta accggctgcc aaagtgtcaa taactggagc agtttcctta gaagcagatt   3540
tcaagtattg gtctctcttg tcttctggga tcaatgtcca caatttgtcc aagttcaaga   3600
ctggcttcca gaaatgagct tgttgcttgt ggaagtatct cataccaacc ttaccgaaat   3660
aacctggatg gtatttatcc atgttaattc tgtggtgatg ttgaccaccg gccatacctc   3720
taccaccggg gtgctttctg tgcttaccga tacgaccttt accggctgag acgtgacctc   3780
tgtgctttct agtcttagtg aatctggaag gcattcttga ttagttggat gattgttctg   3840
ggatttaatg caaaaatcac ttaagaagga aaatcaacgg agaaagcaaa cgccatctta   3900
aatatacggg atacagatga aagggtttga acctatctgg aaaatagcat taaacaagcg   3960
aaaaactgcg aggaaaattg tttgcgtctc tgcgggctat tcacgcgcca gaggaaaata   4020
ggaaaaataa cagggcatta gaaaaataat tttgattttg gtaatgtgtg ggtcctggtg   4080
tacagatgtt acattggtta cagtactctt gtttttgctg tgtttttcga tgaatctcca   4140
aaatggttgt tagcacatgg aagagtcacc gatgctaagt tatctctatg taagctacgt   4200
ggcgtgactt ttgatgaagc cgcacaagag atacaggatt ggcaactgca aatagaatct   4260
ggggatcccc cctcgagatc cgggatcgaa gaaatgatgg taaatgaaat aggaaatcaa   4320
ggagcatgaa ggcaaaagac aaatataagg gtcgaacgaa aaataaagtg aaaagtgttg   4380
atatgatgta tttggctttg cggcgccgaa aaaacgagtt tacgcaattg cacaatcatg   4440
ctgactctgt ggcggacccg cgctcttgcc ggcccggcga taacgctggg cgtgaggctg   4500
tgcccggcgg agtttttttgc gcctgcattt tccaaggttt accctgcgct aaggggcgag   4560
attggagaag caataagaat gccggttggg gttgcgatga tgacgaccac gacaactggt   4620
gtcattattt aagttgccga aagaacctga gtgcatttgc aacatgagta tactagaaga   4680
atgagccaag acttgcgaga cgcgagtttg ccggtggtgc gaacaataga gcgaccatga   4740
ccttgaaggt gagacgcgca taaccgctag agtactttga agaggaaaca gcaatagggt   4800
tgctaccagt ataaatagac aggtacatac aacactggaa atggttgtct gtttgagtac   4860
gctttcaatt catttgggtg tgcactttat tatgttacaa tatggaaggg aactttacac   4920
ttctcctatg cacatatatt aattaaagtc caatgctagt agagaagggg ggtaacaccc   4980
ctccgcgctc ttttccgatt tttttctaaa ccgtggaata tttcggatat ccttttgttg   5040
tttccgggtg tacaatatgg acttcctctt ttctggcaac caaacccata catcgggatt   5100
```

-continued

```
cctataatac cttcgttggt ctccctaaca tgtaggtggc ggaggggaga tatacaatag   5160
aacagatacc agacaagaca taatgggcta aacaagacta caccaattac actgcctcat   5220
tgatggtggt acataacgaa ctaatactgt agccctagac ttgatagcca tcatcatatc   5280
gaagtttcac taccctttt ccatttgcca tctattgaag taataatagg cgcatgcaac   5340
ttcttttctt tttttttctt ttctctctcc cccgttgttg tctcaccata tccgcaatga   5400
caaaaaaaat gatggaagac actaaaggaa aaaattaacg acaaagacag caccaacaga   5460
tgtcgttgtt ccagagctga tgaggggtat cttcgaacac acgaaacttt ttccttcctt   5520
cattcacgca cactactctc taatgagcaa cggtatacgg ccttccttcc agttacttga   5580
atttgaaata aaaaaagttt gccgctttgc tatcaagtat aaatagacct gcaattatta   5640
atcttttgtt tcctcgtcat tgttctcgtt ccctttcttc cttgtttctt tttctgcaca   5700
atatttcaag ctataccaag catacaatca actccaagct tgaagcaagc ctcctgaaag   5760
atgaagctac tgtcttctat cgaacaagca tgcgatattt gccgacttaa aaagctcaag   5820
tgctccaaag aaaaaccgaa gtgcgccaag tgtctgaaga acaactggga gtgtcgctac   5880
tctcccaaaa ccaaaaggtc tccgctgact agggcacatc tgacagaagt ggaatcaagg   5940
ctagaaagac tggaacagct atttctactg atttttcctc gagaagacct tgacatgatt   6000
ttgaaaatgg attctttaca ggatataaaa gcattgttaa caggattatt tgtacaagat   6060
aatgtgaata aagatgccgt cacagataga ttggcttcag tggagactga tatgcctcta   6120
acattgagac agcatagaat aagtgcgaca tcatcatcgg aagagagtag taacaaaggt   6180
caaagacagt tgactgtatc gtcgaggtcg accccgggtg ctagcaaggc cttgtggcca   6240
gccatggcaa ctagtgcggc cgctaagtaa gtaagacgtc gagctctaag taagtaacgg   6300
ccgccaccgc ggtggagctt tggacttctt cgccagaggt ttggtcaagt ctccaatcaa   6360
ggttgtcggc ttgtctacct tgccagaaat ttacgaaaag atggaaaagg gtcaaatcgt   6420
tggtagatac gttgttgaca cttctaaata agcgaatttc ttatgattta tgatttttat   6480
tattaaataa gttataaaaa aaataagtgt atacaaattt taaagtgact cttaggtttt   6540
aaaacgaaaa ttcttgttct tgagtaactc tttcctgtag gtcaggttgc tttctcaggt   6600
atagcatgag gtcgctctta ttgaccacac ctctaccggc atgccgagca aatgcctgca   6660
aatcgctccc catttcaccc aattgtagat atgctaactc cagcaatgag ttgatgaatc   6720
tcggtgtgta ttttatgtcc tcagaggaca atacctgttg taatcgttct tccacacgga   6780
tcccaattcg ccctatagtg agtcgtatta caattcactg gccgtcgttt tacaacgtcg   6840
tgactgggaa aaccctggcg ttacccaact taatcgcctt gcagcacatc ccccttcgc   6900
cagctggcgt aatagcgaag aggcccgcac cgatcgccct tcccaacagt tgcgcagcct   6960
gaatggcgaa tggacgcgcc ctgtagcggc gcattaagcg cggcgggtgt ggtggttacg   7020
cgcagcgtga ccgctacact tgccagcgcc ctagcgcccg ctcctttcgc tttcttccct   7080
tcctttctcg ccacgttcgc cggctttccc cgtcaagctc taaatcgggg gctcccttta   7140
gggttccgat ttagtgcttt acggcacctc gaccccaaaa aacttgatta gggtgatggt   7200
tcacgtagtg ggccatcgcc ctgatagacg gtttttcgcc ctttgacgtt ggagtccacg   7260
ttctttaata gtggactctt gttccaaact ggaacaacac tcaaccctat ctcggtctat   7320
tcttttgatt tataagggat tttgccgatt tcggcctatt ggttaaaaaa tgagctgatt   7380
taacaaaaat ttaacgcgaa ttttaacaaa atattaacgt ttacaatttc ctgatgcggt   7440
```

```
attttctcct tacgcatctg tgcggtattt cacaccgcag gcaagtgcac aaacaatact   7500

taaataaata ctactcagta ataacctatt tcttagcatt tttgacgaaa tttgctattt   7560

tgttagagtc ttttacacca tttgtctcca cacctccgct tacatcaaca ccaataacgc   7620

catttaatct aagcgcatca ccaacatttt ctggcgtcag tccaccagct aacataaaat   7680

gtaagctttc ggggctctct tgccttccaa cccagtcaga aatcgagttc caatccaaaa   7740

gttcacctgt cccacctgct tctgaatcaa acaagggaat aaacgaatga ggtttctgtg   7800

aagctgcact gagtagtatg ttgcagtctt ttggaaatac gagtctttta ataactggca   7860

aaccgaggaa ctcttggtat tcttgccacg actcatctcc atgcagttgg acgatatcaa   7920

tgccgtaatc attgaccaga gccaaaacat cctccttagg ttgattacga aacacgccaa   7980

ccaagtattt cggagtgcct gaactatttt tatatgcttt tacaagactt gaaattttcc   8040

ttgcaataac cgggtcaatt gttctctttc tattgggcac acatataata cccagcaagt   8100

cagcatcgga atctagagca cattctgcgg cctctgtgct ctgcaagccg caaactttca   8160

ccaatggacc agaactacct gtgaaattaa taacagacat actccaagct gcctttgtgt   8220

gcttaatcac gtatactcac gtgctcaata gtcaccaatg ccctccctct tggccctctc   8280

cttttctttt ttcgaccgaa ttaattctta atcggcaaaa aaagaaaagc tccggatcaa   8340

gattgtacgt aaggtgacaa gctatttttc aataaagaat atcttccact actgccatct   8400

ggcgtcataa ctgcaaagta cacatatatt acgatgctgt ctattaaatg cttcctatat   8460

tatatatata gtaatgtcgt ttatggtgca ctctcagtac aatctgctct gatgccgcat   8520

agttaagcca gccccgacac ccgccaacac ccgctgacgc gccctgacgg gcttgtctgc   8580

tcccggcatc cgcttacaga caagctgtga ccgtctccgg gagctgcatg tgtcagaggt   8640

tttcaccgtc atcaccgaaa cgcgcga                                       8667
```

<210> SEQ ID NO 12
<211> LENGTH: 8331
<212> TYPE: DNA
<213> ORGANISM: Artificial Sequence
<220> FEATURE:
<223> OTHER INFORMATION: Description of Artificial Sequence: mutagen

<400> SEQUENCE: 12

```
acgaaagggc ctcgtgatac gcctattttt ataggttaat gtcatgataa taatggtttc     60

ttaggacgga tcgcttgcct gtaacttaca cgcgcctcgt atcttttaat gatggaataa    120

tttgggaatt tactctgtgt ttatttattt ttatgttttg tatttggatt ttagaaagta    180

aataaagaag gtagaagagt tacggaatga agaaaaaaaa ataaacaaag gtttaaaaaa    240

tttcaacaaa aagcgtactt tacatatata tttattagac aagaaaagca gattaaatag    300

atatacattc gattaacgat aagtaaaatg taaaatcaca ggattttcgt gtgtggtctt    360

ctacacagac aagatgaaac aattcggcat taatacctga gagcaggaag agcaagataa    420

aaggtagtat ttgttggcga tccccctaga gtcttttaca tcttcggaaa acaaaaacta    480

ttttttcttt aatttctttt tttactttct atttttaatt tatatattta tattaaaaaa    540

tttaaattat aattattttt atagcacgtg atgaaaagga cccaggtggc acttttcggg    600

gaaatgtgcg cggaacccct atttgtttat ttttctaaat acattcaaat atgtatccgc    660

tcatgagaca ataaccctga taaatgcttc aataatctgc agctctggcc cgtgtctcaa    720

aatctctgat gttacattgc acaagataaa aatatatcat catgaacaat aaaactgtct    780

gcttacataa acagtaatac aaggggtgtt atgagccata ttcaacggga aacgtcttgc    840
```

-continued

```
tggaggccgc gattaaattc caacatggat gctgatttat atgggtataa atgggctcgc    900
gataatgtcg ggcaatcagg tgcgacaatc tttcgattgt atgggaagcc cgatgcgcca    960
gagttgtttc tgaaacatgg caaaggtagc gttgccaatg atgttacaga tgagatggtc   1020
agactaaact ggctgacgga atttatgcct cttccgacca tcaagcattt tatccgtact   1080
cctgatgatg catggttact caccactgcg atccgcggga aaacagcatt ccaggtatta   1140
gaagaatatc ctgattcagg tgaaaatatt gttgatgcgc tggcagtgtt cctgcgccgg   1200
ttgcattcga ttcctgtttg taattgtcct tttaacagcg atcgcgtatt tcgtctcgct   1260
caggcgcaat cacgaatgaa taacggtttg gttgatgcga gtgattttga tgacgagcgt   1320
aatggctggc ctgttgaaca agtctggaaa gaaatgcata cgcttttgcc attctcaccg   1380
gattcagtcg tcactcatgg tgatttctca cttgataacc ttatttttga cgaggggaaa   1440
ttaataggtt gtattgatgt tggacgagtc ggaatcgcag accgatacca ggatcttgcc   1500
atcctatgga actgcctcgg tgagttttct ccttcattac agaaacggct ttttcaaaaa   1560
tatggtattg ataatcctga tatgaataaa ttgcagtttc atttgatgct cgatgagttt   1620
ttctaatcag aattggttaa ttggttgtaa cactggcaga gcattacgct gacttgacgg   1680
gacggcgcat gaccaaaatc ccttaacgtg agttttcgtt ccactgagcg tcagaccccg   1740
tagaaaagat caaaggatct tcttgagatc cttttttttct gcgcgtaatc tgctgcttgc   1800
aaacaaaaaa accaccgcta ccagcggtgg tttgtttgcc ggatcaagag ctaccaactc   1860
tttttccgaa ggtaactggc ttcagcagag cgcagatacc aaatactgtc cttctagtgt   1920
agccgtagtt aggccaccac ttcaagaact ctgtagcacc gcctacatac ctcgctctgc   1980
taatcctgtt accagtggct gctgccagtg gcgataagtc gtgtcttacc gggttggact   2040
caagacgata gttaccggat aaggcgcagc ggtcgggctg aacggggggt tcgtgcacac   2100
agcccagctt ggagcgaacg acctacaccg aactgagata cctacagcgt gagcattgag   2160
aaagcgccac gcttcccgaa gggagaaagg cggacaggta tccggtaagc ggcagggtcg   2220
gaacaggaga gcgcacgagg gagcttccag ggggaaacgc ctggtatctt tatagtcctg   2280
tcgggtttcg ccacctctga cttgagcgtc gatttttgtg atgctcgtca ggggggccga   2340
gcctatggaa aaacgccagc aacgcggcct ttttacggtt cctggccttt tgctggcctt   2400
ttgctcacat gttctttcct gcgttatccc ctgattctgt ggataaccgt attaccgcct   2460
ttgagtgagc tgataccgct cgccgcagcc gaacgaccga gcgcagcgag tcagtgagcg   2520
aggaagcgga agagcgccca atacgcaaac cgcctctccc cgcgcgttgg ccgattcatt   2580
aatgcagctg gcacgacagg tttcccgact ggaaagcggg cagtgagcgc aacgcaatta   2640
atgtgagtta cctcactcat taggcacccc aggctttaca ctttatgctt ccggctccta   2700
tgttgtgtgg aattgtgagc ggataacaat ttcacacagg aaacagctat gaccatgatt   2760
acgccaagct cggaattaac cctcactaaa gggaacaaaa gctggtaccg atcccgagct   2820
ttgcaaatta aagccttcga gcgtcccaaa accttctcaa gcaaggtttt cagtataatg   2880
ttacatgcgt acacgcgtct gtacagaaaa aaaagaaaaa tttgaaatat aaataacgtt   2940
cttaatacta acataactat aaaaaaataa atagggacct agacttcagg ttgtctaact   3000
ccttcctttt cggttagagc ggatgtgggg ggagggcgtg aatgtaagcg tgacataact   3060
aattacatga tatcgacaaa ggaaaagggg cctgtttact cacaggcttt tttcaagtag   3120
gtaattaagt cgtttctgtc tttttccttc ttcaacccac caaaggccat cttggtactt   3180
```

-continued

```
tttttttttt tttttttttt tttttttttt tttttttttt tttttttttt tttttttttt   3240
tttttttttt tttttttttt tttttttttt ttcatagaaa taatacagaa gtagatgttg   3300
aattagatta aactgaagat atataattta ttggaaaata catagagctt tttgttgatg   3360
cgcttaagcg atcaattcaa caacaccacc agcagctctg atttttcttt cagccaactt   3420
ggagacgaat ctagctttga cgataactgg aacatttgga attctaccct tacccaagat   3480
cttaccgtaa ccggctgcca aagtgtcaat aactggagca gtttccttag aagcagattt   3540
caagtattgg tctctcttgt cttctgggat caatgtccac aatttgtcca agttcaagac   3600
tggcttccag aaatgagctt gttgcttgtg gaagtatctc ataccaacct taccgaaata   3660
acctggatgg tatttatcca tgttaattct gtggtgatgt tgaccaccgg ccatacctct   3720
accaccgggg tgctttctgt gcttaccgat acgaccttta ccggctgaga cgtgacctct   3780
gtgctttcta gtcttagtga atctggaagg cattcttgat tagttggatg attgttctgg   3840
gatttaatgc aaaaatcact taagaaggaa aatcaacgga gaaagcaaac gccatcttaa   3900
atatacggga tacagatgaa agggtttgaa cctatctgga aaatagcatt aaacaagcga   3960
aaaactgcga ggaaaattgt ttgcgtctct gcgggctatt cacgcgccag aggaaaatag   4020
gaaaaataac agggcattag aaaaataatt ttgattttgg taatgtgtgg gtcctggtgt   4080
acagatgtta cattggttac agtactcttg tttttgctgt gtttttcgat gaatctccaa   4140
aatggttgtt agcacatgga agagtcaccg atgctaagtt atctctatgt aagctacgtg   4200
gcgtgacttt tgatgaagcc gcacaagaga tacaggattg gcaactgcaa atagaatctg   4260
gggatccccc ctcgacggat gcaagggttc gaatccctta gctctcatta ttttttgctt   4320
tttctcttga ggtsgtcaca tgatcgcaaa atggcaaatg gcacgtgaag ctgtcgatat   4380
tggggaactg tggtggttgg caaatgacta attaagttag tcaaggcgcc atcctcatga   4440
aaactgtgta acataataac cgaagtgtcg aaaaggtggc accttgtcca attgaacacg   4500
ctcgatgaaa aaaataagat atatataagg ttaagtaaag cgtctgttag aaaggaagtt   4560
tttccttttt cttgctctct tgtcttttca tctactattt ccttcgtgta atacagggtc   4620
gtcagataca tagatacaat tctattaccc ccatccatac atctagaact agtggatccc   4680
ccgggctgca ggaattcgat atcaagcttc acagctagcg cactcggtgc cccgcgcagg   4740
gtcgcgatgc tgcccggttt ggcactgttc ctgctggccg cctggacggc tcgggcgctg   4800
gatgcagaat tccgacatga ctcaggatat gaagttcatc atcaaaaatt ggtgttcttt   4860
gcagaagatg tgggttcaaa caaaggtgca atcattggac tcatggtggg cggtgttgtc   4920
atagcgacag tgatcgtcat caccttggtg atgctgaaga agaaacagta cacatccatt   4980
catcatggtg tggtggaggt tgacgccgct gtcaccccag aggagcgcca cctgtccaag   5040
atgcagcaga acggctacga aaatccaacc tacaagttct ttgagcagat gcagaacgcg   5100
cggggtaccc cggcgatgaa gctactgtct tctatcgaac aagcatgcga tatttgccga   5160
cttaaaaagc tcaagtgctc caaagaaaaa ccgaagtgcg ccaagtgtct gaagaacaac   5220
tgggagtgtc gctactctcc caaaaccaaa aggtctccgc tgactagggc acatctgaca   5280
gaagtggaat caaggctaga aagactggaa cagctatttc tactgatttt tcctcgagaa   5340
gaccttgaca tgattttgaa aatggattct ttacaggata taaaagcatt gttaacagga   5400
ttatttgtac aagataatgt gaataaagat gccgtcacag atagattggc ttcagtggag   5460
actgatatgc ctctaacatt gagacagcat agaataagtg cgacatcatc atcggaagag   5520
agtagtaaca aaggtcaaag acagttgact gtatcgccgg aattcccggg gatctgggcc   5580
```

-continued

```
cccccgaccg atgtcagcct gggggacgag ctccacttag acggcgagga cgtggcgatg   5640
gcgcatgccg acgcgctaga cgatttcgat ctggacatgt tgggggacgg ggattccccg   5700
gggccgggat ttacccccca cgactccgcc ccctacggcg ctctggatat ggccgacttc   5760
gagtttgagc agatgtttac cgatgccctt ggaattgacg agtacggtgg gtagggatcc   5820
actagtccag tgtggtggaa ttctgcagat atccagcaca gtggcggccg ctcgaccccg   5880
ggtgctagca aggccttgtg gccagccatg gcaactagtg cggccgctaa gtaagtaaga   5940
cgtcgagctc taagtaagta acggccgcca ccgcggtgga gctttggact tcttcgccag   6000
aggtttggtc aagtctccaa tcaaggttgt cggcttgtct accttgccag aaatttacga   6060
aaagatggaa aagggtcaaa tcgttggtag atacgttgtt gacacttcta aataagcgaa   6120
tttcttatga tttatgattt ttattattaa ataagttata aaaaaaataa gtgtatacaa   6180
attttaaagt gactcttagg ttttaaaacg aaaattcttg ttcttgagta actctttcct   6240
gtaggtcagg ttgctttctc aggtatagca tgaggtcgct cttattgacc acacctctac   6300
cggcatgccg agcaaatgcc tgcaaatcgc tccccatttc acccaattgt agatatgcta   6360
actccagcaa tgagttgatg aatctcggtg tgtattttat gtcctcagag gacaatacct   6420
gttgtaatcg ttcttccaca cggatcccaa ttcgccctat agtgagtcgt attacaattc   6480
actggccgtc gttttacaac gtcgtgactg ggaaaaccct ggcgttaccc aacttaatcg   6540
ccttgcagca catccccctt tcgccagctg gcgtaatagc gaagaggccc gcaccgatcg   6600
cccttcccaa cagttgcgca gcctgaatgg cgaatggacg cgccctgtag cggcgcatta   6660
agcgcggcgg gtgtggtggt tacgcgcagc gtgaccgcta cacttgccag cgccctagcg   6720
cccgctcctt tcgctttctt cccttccttt ctcgccacgt tcgccggctt tccccgtcaa   6780
gctctaaatc gggggctccc tttagggttc cgatttagtg ctttacggca cctcgacccc   6840
aaaaaacttg attagggtga tggttcacgt agtgggccat cgccctgata gacggttttt   6900
cgccctttga cgttggagtc cacgttcttt aatagtggac tcttgttcca aactggaaca   6960
acactcaacc ctatctcggt ctattctttt gatttataag ggattttgcc gatttcggcc   7020
tattggttaa aaaatgagct gatttaacaa aaatttaacg cgaattttaa caaaatatta   7080
acgtttacaa tttcctgatg cggtattttc tccttacgca tctgtgcggt atttcacacc   7140
gcaggcaagt gcacaaacaa tacttaaata aatactactc agtaataacc tatttcttag   7200
catttttgac gaaatttgct attttgttag agtcttttac accatttgtc tccacacctc   7260
cgcttacatc aacaccaata acgccattta atctaagcgc atcaccaaca ttttctggcg   7320
tcagtccacc agctaacata aaatgtaagc tttcggggct ctcttgcctt ccaacccagt   7380
cagaaatcga gttccaatcc aaaagttcac ctgtcccacc tgcttctgaa tcaaacaagg   7440
gaataaacga atgaggtttc tgtgaagctg cactgagtag tatgttgcag tcttttggaa   7500
atacgagtct tttaataact ggcaaaccga ggaactcttg gtattcttgc cacgactcat   7560
ctccatgcag ttggacgata tcaatgccgt aatcattgac cagagccaaa acatcctcct   7620
taggttgatt acgaaacacg ccaaccaagt atttcggagt gcctgaacta tttttatatg   7680
cttttacaag acttgaaatt ttccttgcaa taaccgggtc aattgttctc tttctattgg   7740
gcacacatat aatacccagc aagtcagcat cggaatctag agcacattct gcggcctctg   7800
tgctctgcaa gccgcaaact ttcaccaatg gaccagaact acctgtgaaa ttaataacag   7860
acatactcca agctgccttt gtgtgcttaa tcacgtatac tcacgtgctc aatagtcacc   7920
```

-continued

```
aatgccctcc ctcttggccc tctccttttc ttttttcgac cgaattaatt cttaatcggc   7980

aaaaaaagaa aagctccgga tcaagattgt acgtaaggtg acaagctatt tttcaataaa   8040

gaatatcttc cactactgcc atctggcgtc ataactgcaa agtacacata tattacgatg   8100

ctgtctatta aatgcttcct atattatata tatagtaatg tcgtttatgg tgcactctca   8160

gtacaatctg ctctgatgcc gcatagttaa gccagccccg acacccgcca acacccgctg   8220

acgcgccctg acgggcttgt ctgctcccgg catccgctta cagacaagct gtgaccgtct   8280

ccgggagctg catgtgtcag aggttttcac cgtcatcacc gaaacgcgcg a            8331


<210> SEQ ID NO 13
<211> LENGTH: 355
<212> TYPE: PRT
<213> ORGANISM: Artificial Sequence
<220> FEATURE:
<223> OTHER INFORMATION: Description of Artificial Sequence: mutagen

<400> SEQUENCE: 13

Met Leu Pro Gly Leu Ala Leu Phe Leu Leu Ala Ala Trp Thr Ala Arg
  1               5                  10                  15

Ala Leu Asp Ala Glu Phe Arg His Asp Ser Gly Tyr Glu Val His His
             20                  25                  30

Gln Lys Leu Val Phe Phe Ala Glu Asp Val Gly Ser Asn Lys Gly Ala
         35                  40                  45

Ile Ile Gly Leu Met Val Gly Gly Val Val Ile Ala Thr Val Ile Val
     50                  55                  60

Ile Thr Leu Val Met Leu Lys Lys Lys Gln Tyr Thr Ser Ile His His
 65                  70                  75                  80

Gly Val Val Glu Val Asp Ala Ala Val Thr Pro Glu Glu Arg His Leu
                 85                  90                  95

Ser Lys Met Gln Gln Asn Gly Tyr Glu Asn Pro Thr Tyr Lys Phe Phe
            100                 105                 110

Glu Gln Met Gln Asn Ala Arg Gly Thr Pro Ala Met Lys Leu Leu Ser
        115                 120                 125

Ser Ile Glu Gln Ala Cys Asp Ile Cys Arg Leu Lys Lys Leu Lys Cys
    130                 135                 140

Ser Lys Glu Lys Pro Lys Cys Ala Lys Cys Leu Lys Asn Asn Trp Glu
145                 150                 155                 160

Cys Arg Tyr Ser Pro Lys Thr Lys Arg Ser Pro Leu Thr Arg Ala His
                165                 170                 175

Leu Thr Glu Val Glu Ser Arg Leu Glu Arg Leu Glu Gln Leu Phe Leu
            180                 185                 190

Leu Ile Phe Pro Arg Glu Asp Leu Asp Met Ile Leu Lys Met Asp Ser
        195                 200                 205

Leu Gln Asp Ile Lys Ala Leu Leu Thr Gly Leu Phe Val Gln Asp Asn
    210                 215                 220

Val Asn Lys Asp Ala Val Thr Asp Arg Leu Ala Ser Val Glu Thr Asp
225                 230                 235                 240

Met Pro Leu Thr Leu Arg Gln His Arg Ile Ser Ala Thr Ser Ser Ser
                245                 250                 255

Glu Glu Ser Ser Asn Lys Gly Gln Arg Gln Leu Thr Val Ser Pro Glu
            260                 265                 270

Phe Pro Gly Ile Trp Ala Pro Pro Thr Asp Val Ser Leu Gly Asp Glu
        275                 280                 285

Leu His Leu Asp Gly Glu Asp Val Ala Met Ala His Ala Asp Ala Leu
```

-continued

```
    290                 295                 300

Asp Asp Phe Asp Leu Asp Met Leu Gly Asp Gly Asp Ser Pro Gly Pro
305                 310                 315                 320

Gly Phe Thr Pro His Asp Ser Ala Pro Tyr Gly Ala Leu Asp Met Ala
                325                 330                 335

Asp Phe Glu Phe Glu Gln Met Phe Thr Asp Ala Leu Gly Ile Asp Glu
            340                 345                 350

Tyr Gly Gly
        355
```

Aβ-PEPTIDE SCREENING ASSAY

CROSS-REFERENCE TO RELATED APPLICATIONS

This application is a continuation of U.S. application Ser. No. 09/455,367, filed Dec. 3, 1999, now abandoned, and claims priority under 35 U.S.C. 119 to German application number 189 56 261.6, dated Dec. 7, 1998. All of the above-mentioned applications and all documents cited therein, as well as documents referenced or cited in documents cited herein, are hereby incorporated herein by reference.

FIELD OF THE INVENTION

The invention relates to processes for the determination of the activity of a γ-secretase, individual components of the processes and the use of the processes.

BACKGROUND OF THE INVENTION

Several publications are referenced in this application. These references describe the state of the art to which this invention pertains, and are incorporated herein by reference.

Alzheimer's disease is a neurodegenerative disorder of the brain which is accompanied at the cellular level by a massive loss of neurons in the limbic system and in the cerebral cortex. In the brain areas affected, at the molecular level protein deposits, so-called plaques, can be detected at the molecular level, which are an essential characteristic of Alzheimer's disease. The protein occurring most frequently in these plaques is a peptide 40 to 42 amino acids in size, which is designated as Aβ-peptide. This peptide is a cleavage product of a significantly larger protein of 695 to 770 amino acids, the so-called amyloid precursor protein (APP).

APP is an integral transmembrane protein which firstly traverses the lipid bilayer. By far the largest part of the protein is extracellular, while the shorter C-terminal domain is directed into the cytosol (FIG. 1). The Aβ-peptide is shown dark-gray in FIG. 1. About two thirds of the Aβ-peptide originates from the extracellular domain and about one third from the transmembrane domain of APP.

Beside the membrane-based APP, a secreted form of the amyloid precursor protein can be detected which consists of the large ectodomain of the APP and is designated as $APP_{sec}$ ("secreted APP"). $APP_{sec}$ is formed from APP by proteolytic cleavage, which is effected by the α-secretase. The proteolytic cleavage takes place in a site of the amino acid sequence of APP which is within the amino acid sequence of the Aβ-peptide (after amino acid residue 16 of the Aβ-peptide). Proteolysis of APP by the α-secretase thus excludes the formation of the Aβ-peptide.

The Aβ-peptide can thus only be formed from APP in an alternative processing route. It is postulated that two further proteases are involved in this processing route, one protease, which is designated as β-secretase, cleaving at the N-terminus of the Aβ-peptide in the APP and the second protease, which is designated as γ-secretase, releasing the C-terminus of the Aβ-peptide (Kang, J. et al., Nature, 325, 733) (FIG. 1).

Up to now, it has not been possible to identify any of the three secretases or proteases (α-secretase, β-secretase, γ-secretase). Knowledge of the secretases, however, is of great interest, in particular in the context of investigations on Alzheimer's disease and for the identification of the proteins involved, which can then in turn be employed as targets in continuing studies. On the one hand, the inhibition of the β-secretase and in particular of the γ-secretase could lead to a reduction in the Aβ-production, on the other hand an activation of the α-secretase could increase the processing of APP in APPsec and would thus simultaneously reduce the formation of the Aβ-peptide. A transgenic *C. elegans* which is found in the course of such investigations is described in the unpublished German Patent Application having the reference 198 49 073.9.

There are many indications of the fact that the Aβ-peptide is a crucial factor in the occurrence of Alzheimer's disease. Inter alia, neurotoxicity of Aβ-fibrils in cell culture is postulated (Yankner, B. A. et al., (1990) Proc Natl Acad Sci USA, 87, 9020). In patients with Down's syndrome, in which APP occurs in an additional copy, the neuropathology characteristic of Alzheimer's disease also occurs even at an age of 30 years. Here, it is assumed that the overexpression of APP follows an increased conversion into the Aβ-peptide (Rumble, B. et al., (1989), N. Engl. J. Med., 320, 1446).

Perhaps the strongest indication of the central role of the Aβ-peptide are the familial forms of Alzheimer's disease. Here, mutations are found in the APP gene around the area of the β and γ-secretase cleavage sites or in two further AD-associated genes (presenilins), which in cell culture lead to a significant increase in Aβproduction (Scheuner, D. et al., (1996), Nature Medicine, 2, 864).

There are a number of indications of the fact that APP is first cleaved into the Aβ-peptide by the β-secretase during its processing in order, following this, to serve as a substrate for γ-secretase (Maruyama, K. Y. et al., (1994) Biochem. Biophys Res Commun, 202, 1517; Estus, S. et al., (1992), Science, 255, 726). The γ-secretase therefore has a crucial role in the formation of the Aβ-peptide. A demonstration of the activity of the γ-secretase which is customarily used is the detection of the Aβ-peptide, which, however, frequently turns out to be difficult.

An important reason for this is that only a small part of APP is converted into the Aβ-peptide (Simons M, et al., Neurosci (1996) 1;16(3):899–908). Moreover, the Aβ-peptide is an only very small breakage fragment of about 4 kDa and, on account of its hydrophobic character, has a great tendency to self-aggregation so that it easily precipitates under physiological conditions (Hilbich, C. et al., (1991) J. Mol. Biol., 218, 149).

The detection of the Aβ-peptide in eukaryotic cells is carried out by means of immunobiological methods such as, for example, ELISA, immunoprecipitation and Western blofting (Suzuki, N. et al., Science 1994, 27, 264(5163) 1336; Haass, C. et al., (1992) Nature, 359, 322). These processes are relatively laborious, as they involve incubation with appropriate antibodies and necessitate destruction of the cells used, which are obtained from cell culture or model organisms (inter alia *C. elegans*).

SUMMARY OF THE INVENTION

The present invention relates to a novel process for the determination of the γ-secretase activity and for the detection of γ-secretase; particular embodiments of the process relate on the one hand to processes for the identification of a γ-secretase or of a cDNA which codes for a γ-secretase and on the other hand to processes for the identification of substances which can inhibit the activity of a γ-secretase. Such substances have particular importance, as they can be used, for example, as pharmaceutical active compounds, e.g for the treatment of Alzheimer's disease.

DETAILED DESCRIPTION OF THE

INVENTION

The present invention relates to a process for the detection of γ-secretase, where 1. a transgene is used which encodes a fusion protein and contains the following constituents:
   a) a first nucleotide sequence which codes for a protein which contains the amino acid sequence GAIIGLMVGGVVIATVIVITLVML (SEQ ID NO. 1),
   b) at the 5' end of the first nucleotide sequence, a second nucleotide sequence which codes for a signal peptide,
   c) a promoter and,
   d) if appropriate, further coding and/or noncoding nucleotide sequences;
2. this transgene is incorporated into a cell and the fusion protein is expressed;
3. the fusion protein is cleaved within the amino acid sequence SEQ ID NO. 1 by γ-secretase present in the cell, whereby a first partial protein, which contains the amino acid sequence GAIIGLMVGGVV (SEQ ID NO. 2), and a second partial protein, which contains the amino acid sequence VIVITLVML (SEQ ID NO. 3), are formed; and
4. the first partial protein and/or the second partial protein are detected.

The invention also relates to a process for the detection of the activity of γ-secretase, where 1. a transgene is prepared/used which encodes a fusion protein and contains the following constituents:
   a) a first nucleotide sequence which codes for a protein which contains the amino acid sequence GAIIGLMVGGVVIATVIVITLVML (SEQ ID NO. 1),
   b) at the 5' end of the first nucleotide sequence, a second nucleotide sequence which codes for a signal peptide,
   c) a promoter and,
   d) if appropriate, further coding and/or noncoding nucleotide sequences;
2. this transgene is incorporated into a cell and the fusion protein is expressed;
3. the fusion protein is cleaved within the amino acid sequence SEQ ID NO. 1 by γ-secretase present in the cell, whereby a first partial protein, which contains the amino acid sequence GAIIGLMVGGVV (SEQ ID NO. 2), and a second partial protein, which contains the amino acid sequence VIVITLVML (SEQ ID NO. 3), are formed; and
4. the amount of second partial protein is determined and the activity of the γ-secretase is determined from the amount of second partial protein formed.

Figure 2:
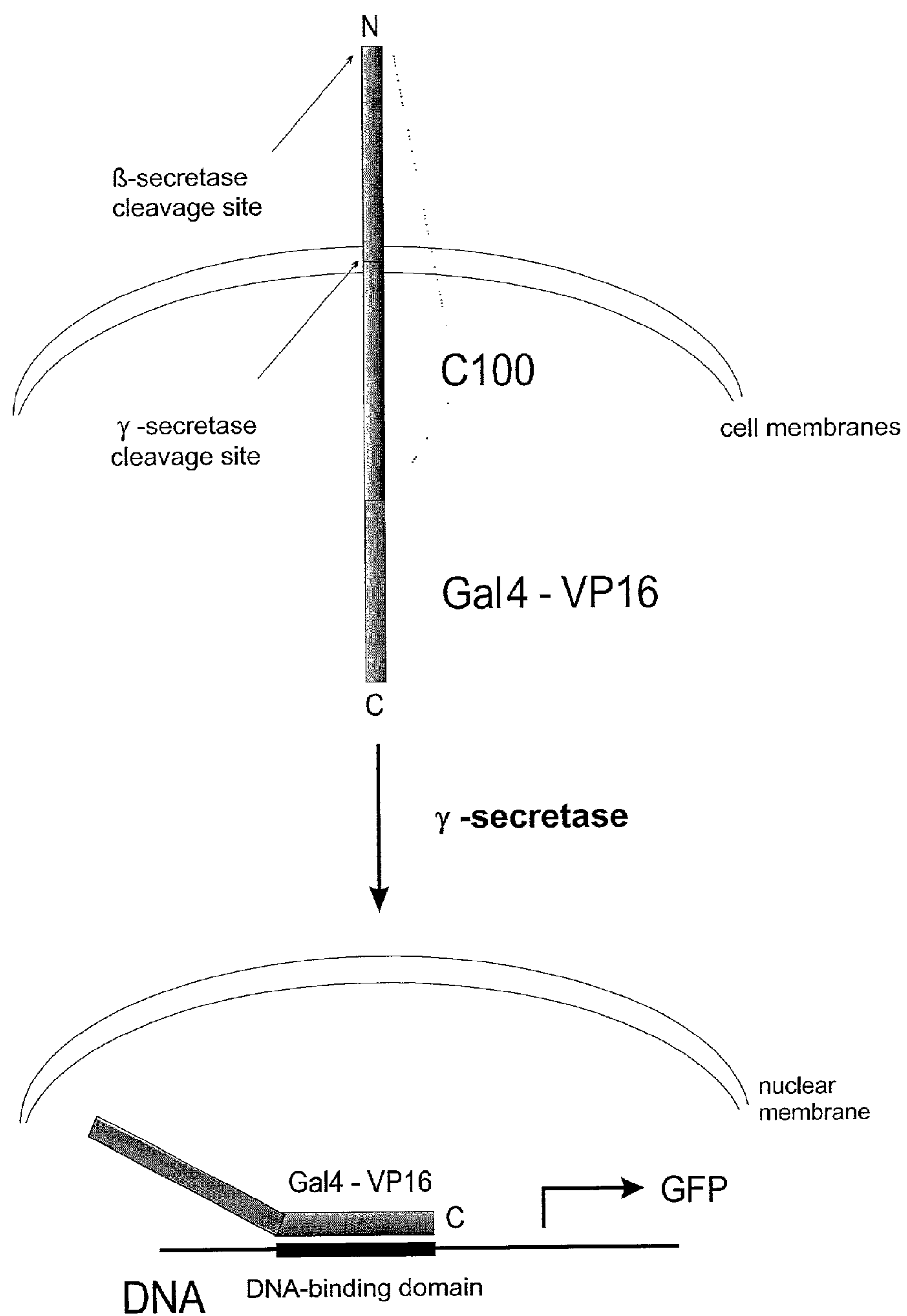

The processes ("Aβ-peptide screening assay", "γ-secretase assay") are suitable for the in vivo detection of a γ-secretase or of the activity of a γ-secretase, it being possible to employ the processes universally, even, for example, in high throughput screening ("HTS"). The processes do not have the above mentioned disadvantages of conventional detection processes, in particular, laborious isolation and detection steps are not necessary. The basis of the processes is that the C-terminal APP fragment is cleaved by the γ-secretase into two fragments—a first partial protein which contains the amino acid sequence GAIIGLMVGGVV (SEQ ID NO. 2) and a second partial protein which contains the amino acid sequence VIVITLVML (SEQ ID NO. 3), and the second partial protein containing the amino acid sequence VIVITLVML (SEQ ID NO. 3) diffuses into the cytosol of the cell (FIG. 2). This second partial protein can be easily detected in the cytosol of a cell, for example, with the aid of a reporter gene, and it serves as a detection for a γ-secretase or the activity of a γ-secretase. The γ-secretase cleavage site is located in the transmembrane domain of the APP (Kang, J. et al., (1987) Nature, 325, 733). The APP transmembrane domain has the amino acid sequence GAIIGLMVGGVV$_{40}$ IA$_{42}$ TVIVITLVML (SEQ ID NO: 1). The γ-secretase cleaves after $V_{40}$, $A_{42}$ or $T_{43}$. In contrast to this, the Aβ-peptide, which is produced by eukaryotic cells in cell culture, is secreted into the medium supernatant.

With the aid of a suitable reporter system, the release of the second partial protein can activate the expression of a reporter protein which can be detected in eukaryotic cells. By means of the detection of the reporter protein, it can be demonstrated that a γ-secretase cleavage has taken place in the APP. As a result, the γ-secretase or the activity of the γ-secretase can be determined qualitatively and/or quantitatively.

The constituents of the process can be characterized in greater detail as follows:

The first nucleotide sequence codes for an amyloid precursor protein (APP) or a part thereof. Preferably, the first nucleotide sequence codes for a protein which contains the amino acid sequence SEQ ID NO. 4 (SEQ ID NO. 4 contains SEQ ID NO. 1).

The second nucleotide sequence codes for a signal peptide, preferably for the signal peptide of APP (subsequently abbreviated "SP"). The signal peptide contains, for example, the amino acid sequence SEQ ID NO. 5.

As a promoter, it is possible to use a regulatable or a constitutive promoter. The promoter can be suitable, for example, for expression in mammalian cells, in *C. elegans,* in yeast or in *Drosophila.* Suitable promoters for mammalian cells are, for example, CMV (e.g: Clontech, Heidelberg, Germany), HSV TK (e.g. Clontech), RSV (e.g. Invitrogen, NV Leek, Netherlands), SV40 (e.g. Clontech) and LTR (e.g. Clontech). Promoters which can be used for *C. elegans* are, for example, unc119, unc54, hspl 16-2, $G_0$A1 and sel-12. For expression in yeast, the promoters ADH1 (constitutive) (Vlckova et al. (1994) Gene, 25(5), 472–4), Gal 1 (conditionally inducible) (Selleck et al. (1987) Nature 325, 173–7), MET3 (conditional) (Cherest et al. (1987) Mol Gen Genet 210, 307–13) and Met 25 are suitable. In *Drosophila,* it is possible to use, for example, the promoters MT (metallothionine) (e.g. Invitrogen), Ac5 (Invitrogen) or Ds47 (Invitrogen).

Preferably, a eukaryotic cell is employed in the process, for example a human cell or a nonhuman cell, e.g. monkey, hamster, mouse, *Drosophila,* Zebrafish or yeast. For example, an HeLa, 293, H4, SH-SY5Y, H9, Cos, CHO, N2A, SL-2 or *Saccharomyces cerevisiae* cell can be employed. In a particular embodiment of the invention a *C. elegans* cell is employed. The cell can be a constituent of a transgenic, nonhuman animal. In a particular embodiment, the transgenic cell can be a constituent of a transgenic *C. elegans.* In particular, the invention relates to processes in which yeast cells, e.g. from the strain MAV203 (Life Technologies, Rockville, Md., USA) or EGY 48 (OriGene Technologies, Inc. Rockville, Md., USA), are used.

The transgene codes for a fusion protein; this is composed of the partial proteins which are encoded by the first and the second nucleotide sequence and, if appropriate, further nucleotide sequences. The fusion protein thus contains the first partial protein and the second partial protein and, if appropriate, a further partial protein. The fusion protein, for example, has the amino acid sequence SEQ ID NO. 6.

In particular, a transgene which has the nucleotide sequence SEQ ID NO. 8 can be employed in the process. In particularly preferred embodiments of the process, the transgene is present in a vector. The recombinant vector can have the nucleotide sequence SEQ ID NO. 9. This special embodiment of the invention is also designated as a SP-C100-Gal 4-VP16 system. In this case, a fusion protein consisting of the signal peptide of APP, the C100 fragment of APP, Gal4 and VP16 is expressed. This protein located in the transmembrane domain is cleaved within the C100 fragment and the second partial protein, i.e. the part of the fusion protein which contains one part of the C 100 fragment, Gal4 and VP16, is detected with the aid of a reporter plasmid.

Beside the transgene construct SPC100-Gal4-VP16, other reporter constructs are also conceivable in which, for example, the transcription-activating domain could be inserted between the transmembrane domain and cytosolic domain of SPC100 or a Tag (e.g. MYC, FLAG) on the N- and C-terminus and between the transmembrane and the cytosolic domain of SPC100.

The further coding nucleotide sequence can code, for example, for a protein which can be used for the detection of the second partial protein. Preferably, the further coding nucleotide sequence is therefore located at the 3' end of the first nucleotide sequence. The further coding nucleotide sequence codes, for example, for a chimeric protein or another protein which is constructed from a number of domains, e.g. a protein which contains a DNA-binding domain and a transcription-activating domain. In a particular embodiment of the invention, the further coding nucleotide sequence codes for a protein which consists of a Gal4-binding domain and of the transcription-activating domain of VP16 (Gal4-VP 16), and the further partial protein preferably then has the amino acid sequence SEQ ID NO. 7. In yeast cells, the further partial protein can also contain a LexA-binding domain (e.g. Lex A-VP16). This further partial protein is particularly suitable for processes in which cells of the yeast strain EGY48 are used.

In particular, the invention relates to processes in which cells are used which are cotransfected with a reporter plasmid. The reporter plasmid contains a reporter gene under the control of a regulatable promoter. For example, the reporter gene can code for GFP and its derivatives, e.g. EGFP (Enhanced Green Fluorescent Protein), EBFP, EYFP, d2EGFP, GFPuv or Luciferase (e.g. Promega, Mannheim, Germany), CAT (e.g. Promega), SEAP (e.g. Clontech), βGal (e.g. Clontech) or apoptosis-inducing factors, e.g. Fas, TNF-R1, death domain and homologs (Tartaglia et al. (1993) Cell 74, 845–53), ced3, ced4, ced9. As a regulatable promoter, the reporter plasmid can contain, for example, a minimal promoter of HIV, of the CD4 promoter or the mec7 promoter. The choice of the suitable regulatable promoter depends on the transcription-activating domain used.

A particular embodiment of the invention relates to the implementation of the process, where the cells used are yeast cells. As an alternative to the yeast expression vector pDB-TRP (Life Technologies Inc., Rockville, Md, USA) (SEQ ID NO.: 11) into which in a special embodiment of the invention a MET-25 promotor is integrated (e.g. SEQ ID NO. 12), a large number of other expression vectors with different promoters (e.g. the inducible Gal1-promoter, the constitutively active ADH1 promoter) and with different selection markers (ADE, LEU, TRP, HIS, LYS, PHE) can be selected.

A particular embodiment of the invention relates to the use of yeast cells which contain Gal4- or LexA-inducible reporter genes either stable integrated in their genome or extrachromosomal. In this embodiments preferably the yeast strains MaV203 (Life Technologies Inc.) or EGY48 (Ori-Gene Technologies, Inc., Rockville, Md. USA) are used.

A particular embodiment of the processes relates to the use of a cell which was additionally transfected with a further recombinant vector. Preferably, the cell which is used for these embodiments normally has no or hardly any endogenous γ-secretase or endogenous γ-secretase activity and is not detectable using the abovementioned processes. This cell can be employed transformed with a further vector in which a nucleotide sequence—preferably a cDNA—is contained which codes for a γ-secretase. For example, a cDNA bank can be employed. This embodiment of the process can then be used, inter alia, to identify a γ-secretase or a cDNA which codes for a γ-secretase. cDNA banks which can be searched for a γ-secretase can be prepared from cells or tissues, e.g. B cells, neurons, glia cells, hippocampus whole brain, placenta, kidney. Preferably, the cDNA is prepared from human cells or human tissues but also from other organisms (e.g. hamster, rat, mouse, dog, monkey).

In the case of cells which without transfection exhibit no γ-secretase activity, but after transfection with a cDNA bank exhibit γ-secretase activity, the cDNA present in the cell codes for a γ-secretase. This cDNA can be isolated by known processes from cells which exhibit this behavior and further be analyzed by known methods.

The invention also relates to a transgene which codes for a fusion protein and contains the following constituents:

a) a first nucleotide sequence which codes for a protein which contains the amino acid sequence GAIIGLM-VGGVVIATVIVITLVML (SEQ ID NO. 1),
b) at the 5' end of the first nucleotide sequence, a second nucleotide sequence which codes for a signal peptide,
c) a promoter and
d) at least one further nucleotide sequence at the 3' end of the first nucleotide sequence, which codes for a DNA-binding domain and for a transcription-activating domain.

Preferably, the first nucleotide sequence codes for APP or a part of APP. The transgene can, for example, have the nucleotide sequence SEQ ID NO. 8. The transgene can be present in a vector. This can, for example, have the nucleotide sequence SEQ ID NO. 9.

The process relates to the use of a transgene and/or of a vector for the production of a transgenic cell, it being possible for the cell to be a constituent of a nonhuman organism. For example, the transgene and/or the vector can be used for the production of a transgenic *C. elegans*. In another particular embodiment, the transgene and/or the vector is used for the production of transgenic yeast cells, e.g. *S. cerevisiae* cells.

The invention also relates to a process for the production of a nonhuman organism, e.g. of a transgenic *C. elegans*, where a transgene and/or a vector which contains a transgene is microinjected into the gonads of the organism, i.e., for example, of a *C. elegans*. The invention also relates to a cell which contains a transgene according to the invention and a transgenic *C. elegans* which contains a transgene according to the invention. The invention also relates to a cell, in particular a yeast cell, which contains a transgene according to the invention, preferably present in a suitable vector. The invention relates in particular to cells, preferably yeast cells, which contain the transgene according to the invention and additionally a cDNA bank.

The invention relates to the use of transgenic or recombinant cells, preferably yeast cells, or of a transgenic *C. elegans* in a process for the determination of γ-secretase, or the activity of γ-secretase, the use of these cells or of a transgenic *C. elegans* in a process for the identification of inhibitors of the activity of the γ-secretase, and the process itself.

In particular, the invention relates to processes for the identification of substances which inhibit the activity of a γ-secretase, the process containing the following process steps:

1. Production of a transgenic nonhuman organism, e.g. of a transgenic *C. elegans* or *Saccharomyces cerevisiae* or of a transgenic cell, the transgenic nonhuman organism or the transgenic cell containing a transgene which has the following constituents:
   a) a first nucleotide sequence which codes for a protein which contains the amino acid sequence GAIIGLMVGGVVIATVIVITLVML (SEQ ID NO. 1),
   b) at the 5' end of the first nucleotide sequence, a second nucleotide sequence which codes for a signal peptide and
   c) a promoter and the transgenic nonhuman organism or the transgenic cell moreover contains a reporter plasmid, the reporter plasmid carrying a protein binding site, a minimal promoter and a reporter gene and, if appropriate, a cDNA which encodes a γ-secretase, where the transgenic nonhuman organism or the transgenic cell expresses the transgene and, if appropriate, the γ-secretase encoded by the cDNA;
2. the transgenic nonhuman organism or the transgenic cell is incubated with a substance to be investigated; and
3. the amount of second partial protein is detected.

The invention also relates to a process for the identification of substances which inhibit the activity of the γ-secretase, where 1. a transgene is prepared/used which contains the following constituents:
   a) a first nucleotide sequence which codes for a protein which contains the amino acid sequence GAIIGLMVGGVVIATVIVITLVML (SEQ ID NO. 1),
   b) at the 5' end of the first nucleotide sequence, a second nucleotide sequence which codes for a signal peptide and
   c) a promoter and,
   d) if appropriate, further coding and/or noncoding nucleotide sequences;
2. this transgene and a reporter plasmid and, if appropriate, a cDNA which codes for a γ-secretase are incorporated into a cell and the fusion protein encoded by the transgene and, if appropriate, the γ-secretase encoded by the cDNA are expressed in the presence of a substance to be investigated,
3. the fusion protein is
   a) cleaved or
   b) not cleaved within the amino acid sequence SEQ ID NO. 1 by γ-secretase present in the cell, as a result of which either
   c) a first partial protein which contains the amino acid sequence GAIIGLMVGGVV (SEQ ID NO. 2) and a second partial protein which contains the amino acid sequence VIVITLVML (SEQ ID NO. 3) are formed, or
   d) no detectable amount of first and/or second partial protein is formed,
4. it is determined whether a second partial protein was formed.

The invention also relates to processes for the identification of substances which inhibit the activity of a γ-secretase, where a transgene which codes for a protein which contains a signal peptide and the SEQ ID NO. 1 is expressed in the presence of a substance to be investigated and of a reporter plasmid and the effect of the substance to be investigated on the amount of second partial protein formed is determined, the second partial protein containing the amino acid sequence VIVITLVML (SEQ ID NO. 3).

The invention also relates to inhibitors of a γ-secretase which are identified by the processes.

Inter alia, the processes can be used, for example, in conjunction with the C100-Gal 4-VP16 system (i.e. a fusion protein consisting of C100, Gal4 and VP16 or using a nucleic acid which codes for a corresponding fusion protein) for:

1. Identification and determination (qualitative and/or quantitative) of the activity of a γ-secretase.
2. Identification of γ-secretases in different tissues, cells and organisms or species. Identification and isolation of the cDNAs concerned which code for this γ-secretase and the further use of the cDNAs.
3. Screening in vivo, e.g. in yeast cells (e.g. *Saccharomyces cerevisiae*) or in *C. elegans,* it being possible to determine the activity of the γ-secretase without use of immunobiological methods.
4. Use of the process for the identification and characterization of substances, e.g. pharmacological active compounds, which modulate the activity of the γ-secretase, e.g. inhibitors of the γ-secretase. In particular, this process can be employed in an HTS (High Throughput Screening). For example, substances can be identified which can be employed for the treatment of Alzheimer's disease and/or for preventive treatment.
5. Investigations in the context of Alzheimer's disease, e.g. with mutated APP or C100.
6. The described fusion proteins/transgenes, e.g. C100 in SP-C100-Gal 4-VP16, can be replaced by whole APP and the γ-secretase, its activity and regulation can likewise be investigated with the aid of the processes.

DETAILED DESCRIPTION OF THE FIGURES

FIG. 1: FIG. 1 shows the amyloid precursor protein (Isoform APP695 and Isoforms APP770 or APP751) and secretase cleavage products.

FIG. 2: Shows schematically the principle on which the processes are based:

β-secretase cleavage site at the N-terminus; γ-secretase cleavage site in the transmembrane domain; C100=C100 fragment of APP; Gal4-VP16=DNA-binding domain, transcription-activating domain (consisting of DNA-binding domain and transcription activator), which binds to the protein-binding domain on the DNA of the reporter plasmid.

Figure 3:
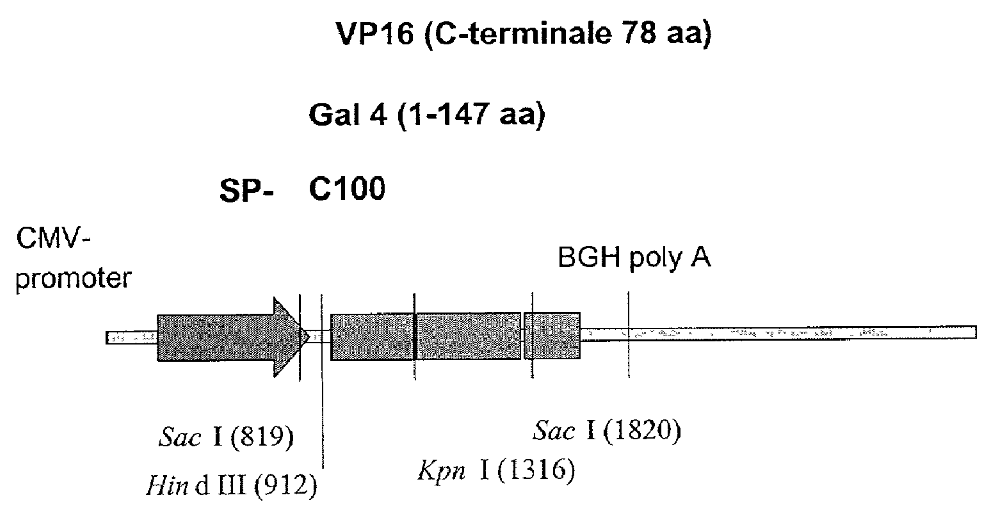

FIG. 3: Construction of the expression plasmids SP-C100-Gal4-VP16:

aa=amino acids; restriction cleavage sites Sac I, Hind III and Kpn I indicating the position of the cleavage site on the plasmid.

Figure 4:
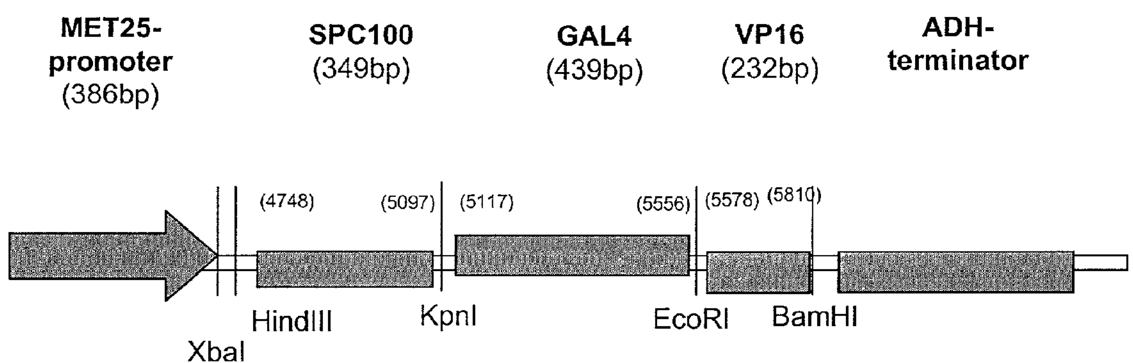

FIG. 4: Expression plasmid pDBTRP-MET25-SP-C100-Gal4-VP16:

Construction of the expression plasmid for the expression of the transgene in yeast.

EXAMPLES

The following examples are illustrative of some of the products and compositions and methods of making and using the same falling within the scope of the present invention.

Example 1

Construction of the Expression Plasmid SP-C100-Gal4-VP16

The plasmid encodes the APP signal peptide (SP) which is fused to the C-terminal 100 amino acid residues of APP (C100). C100 begins with the N-terminus of the Aβ-peptide and ends with the C-terminus of APP. It must additionally be cleaved by the Aγ-secretase in order to release the Aβ-peptide.

Gal4-VP16 was fused to the C-terminus of SP-C100. Gal4-VP16 is composed of the first 147 amino acid residues of the yeast transcription activator Gal4 and the 78 C-terminal amino acid residues of VP 16, a transcription activator from the herpes simplex virus. As a fusion protein, the Gal 4 fragment takes over the function of the DNA binding while the VP16 fragment activates the transcription (Sadowski et al., (1988) Science 335, 563). pcDNA3.1+from Invitrogen, Netherlands, serves as a vector plasmid.

Example 2

Construction of the Reporter Plasmid pGL2 MRG5 EGFP

The reporter plasmid pGL2 MRG5 has five Gal 4 binding sites ahead of the HIV-TATA box. For easier detection in cell culture, the luciferase gene was exchanged for the gene for EGFP (Enhanced Green Fluorescent Protein) from the vector pEGFP N1 from Clontech, Heidelberg.

Example 3

Human neuroblastoma cells (SH-SY5Y cells) were cotransfected with both plasmids and then microscopically analyzed under irradiation with light of wavelength 480 nm, by means of which EGFP is excited. In some cases, it was possible to detect cells luminescing a strongly green color.

Since this effect could also be based on expression of the EGFP by the reporter plasmid without specific activation, SH-SY5Y cells were transfected only with reporter plasmid. In these cells, no green fluorescence was detectable. The expression must therefore be activated by Gal4-VP16, which presupposes a proteolytic release of the APP-C terminus. Until now, apart from γ-secretase, no further proteolytic activities had been described which proteolytically process APP within the transmembrane domain or in the cytoplasmic part. It is therefore assumed that the release of the APP-C terminus, fused to Gal 4-VP16, is based on the activity of the γ-secretase.

Example 4

Use of the C 100-Gal4-VP16 system for the detection of a cDNA coding for a γ-secretase activity in cDNA banks:

SPC 100-Gal4-VP 16 was cloned in the yeast expression vector pDBTRP (Life Technologies Rockville, Md, U.S.A.) under control of the MET25 promoter and the yeast strain MaV203 (Life Technologies) was transformed using these constructs. The yeast strain MaV203 is genetically modified and contains three GAL4-inducible reporter genes (URA3, HIS3, LacZ), which are stably integrated into the genome. The expression of the SPC 100-Gal4-VP16 cDNA in MaV203 afforded only a small activity of the reporters, such that this system is suitable for a search for a γ-secretase in a cDNA bank.

Example 5

The recombinant MaV203 cells from Example 4 can be used, for example, for the identification of γ-secretases or screening of a human B cell cDNA bank (American Type Culture Collection, Manassas, Va., U.S.A.). Analogously, a human hippocampal cDNA bank, integrated into the yeast expression vectors p415-MET25 (ATCC, Nucleic Acid Research, 1994, Vol. 22, No. 25, 5767) or p415-ADH1 (ATCC, GENE, 1995,158: 119–122), could also be employed for screening for a cDNA which codes for a γ-secretase or a protein having γ-secretase activity.

The above description of the invention is intended to be illustrative and not limiting. Various changes or modifications in the embodiments described may occur to those skilled in the art. these can be made without departing from the spirit or scope of the invention.

I claim:

1. A process for detecting the presence of γ-secretase in a cell in vitro, comprising:

a) transforming the cell with a nucleic acid encoding a fusion protein having (i) a first amino acid sequence comprising GAIIGLMVGGVVIATVIVITLVML (SEQ ID NO. 1); wherein said first amino acid sequence comprises a transmembrane domain; (ii) a signal peptide fused to the N-terminal end of the first amino acid sequence, and (iii) a protein located at the C-terminal end of the first amino acid sequence and containing a DNA-binding domain and a transcription-activating domain, wherein the fusion protein is expressed in the cell, and whereby if γ-secretase is present in the cell, the fusion protein is cleaved into a first partial protein containing amino acid sequence GAIIGLMVGGVV (SEQ ID NO. 2), and a second partial protein containing amino acid sequence VIVITLVML (SEQ ID NO. 3);

b) transforming the cell with a reporter gene under the control of a regulatable promoter, wherein protein of (iii) regulates the promoter; and c) detecting the presence of the first partial protein and/or the second partial protein by detecting expression of the reporter gene, thereby detecting γ-secretase activity, and thus, the presence of γ-secretase in the cell.

2. A process for detecting γ-secretase activity in vitro in a cell containing γ-secretase, comprising:

a) transforming the cell with a nucleic acid encoding a fusion protein having (i) a first amino acid sequence comprising GAIIGLMVGGVVIATVIVITLVML (SEQ ID NO. 1); wherein said first amino acid sequence comprises a transmembrane domain; (ii) a signal peptide fused to the N-terminal end of the first amino acid sequence, and (iii) a protein located at the C-terminal end of the first amino acid sequence and containing a DNA-binding domain and a transcription-activating domain, wherein the fusion protein is expressed in the cell, and whereby the fusion protein is cleaved into a first partial protein containing amino acid sequence GAIIGLMVGGVV (SEQ ID NO. 2), and a second partial protein containing amino acid sequence VIVITLVML (SEQ ID NO. 3);

b) transforming the cell with a reporter gene under the control of a regulatable promoter, wherein the protein of (iii) regulates the promoter; and c) determining the amount of second partial protein in the cell by detecting expression of the reporter gene, thereby detecting γ-secretase activity.

3. The process as claimed in claim 1, wherein the first amino acid sequence is an amyloid precursor protein (APP) or a part thereof.

4. The process as claimed in claim 2, wherein the first amino acid sequence is an amyloid precursor protein (APP) or a part thereof.

5. The process as claimed in claim 1, wherein the first amino acid sequence has the amino acid sequence of SEQ ID NO. 4.

6. The process as claimed in claim 2, wherein the first amino acid sequence has the amino acid sequence of SEQ ID NO. 4.

7. The process as claimed in claim 1, wherein the signal peptide is the signal peptide of APP (SP).

8. The process as claimed in claim 2, wherein the signal peptide is the signal peptide of APP (SP).

9. The process as claimed in claim 1, wherein the signal peptide has the amino acid sequence of SEQ ID NO. 5.

10. The process as claimed in claim 2, wherein the signal peptide has the amino acid sequence of SEQ ID NO. 5.

11. The process as claimed in claim 1, wherein the fusion protein is under the control of a promoter for expression in mammalian cells, in *C. elegans,* in yeast or in *Drosophila.*

12. The process as claimed in claim 2, wherein the fusion protein is under the control of a promoter for expression in mammalian cells, in *C. elegans,* in yeast or in *Drosophila.*

13. The process as claimed in claim 1, wherein the fusion protein is under the control of a promoter selected from the group consisting of CMV, HSV TK, RSV, SV40, LTR, unc119, unc54, hsp16-2, $G_0$A1, sel-12, ADH1, Gal1, MET3, MET25, MT, Ac5 and Ds47.

14. The process as claimed in claim 2, wherein the fusion protein is under the control of a promoter selected from the group consisting of CMV, HSV TK, RSV, SV40, LTR, unc119, unc54, hsp16-2, $G_0$A1, sel-12, ADH1, Gal1, MET3, MET25, MT, Ac5 and Ds47.

15. The process as claimed in claim 1, wherein the cell is a eukaryotic cell.

16. The process as claimed in claim 2, wherein the cell is a eukaryotic cell.

17. The process as claimed in claim 1, wherein the cell is a human cell.

18. The process as claimed in claim 2, wherein the cell is a human cell.

19. The process as claimed in claim 1, wherein the cell is a nonhuman cell.

20. The process as claimed in claim 2, wherein the cell is a nonhuman cell.

21. The process as claimed in claim 15, wherein the cell is selected from the group consisting of a HeLa, 293, H4, SH-SY5Y, H9, Cos, CHO, N2A, SL-2 and *Saccharomyces cerevisiae*.

22. The process as claimed in claim 16, wherein the cell is selected from the group consisting of a HeLa, 293, H4, SH-SY5Y, H9, Cos, CHO, N2A, SL-2 and *Saccharomyces cerevisiae*.

23. The process as claimed in claim 19, wherein the cell is a *C. elegans* cell.

24. The process as claimed in claim 20, wherein the cell is a *C. elegans* cell.

25. The process as claimed in claim 19, wherein the cell is a yeast cell.

26. The process as claimed in claim 1, wherein the fusion protein contains the amino acid sequence of SEQ ID NO. 6.

27. The process as claimed in claim 2, wherein the fusion protein contains the amino acid sequence of SEQ ID NO. 6.

28. The process as claimed in claim 3, wherein the DNA-binding domain is a Gal4-binding domain and the transcription-activating domain is a of VP16 transcription-activating domain (Gal4-VP16).

29. The process as claimed in claim 1, wherein the reporter gene encodes EGFP (Enhanced Green Fluorescent Protein), Ura 3, His 3 or Lac Z, and wherein the regulatable promoter contains Gal4 binding sites and a minimal promoter of HIV.

30. The process as claimed in claim 1, wherein the first amino acid sequence is encoded by the nucleotide sequence of SEQ ID NO. 8.

31. The process as claimed in claim 2, wherein the first amino acid sequence is encoded by the nucleotide sequence of SEQ ID NO. 8.

32. The process as claimed in claim 1, wherein the cell is transformed with a recombinant vector comprising a nucleic acid molecule encoding the fusion protein.

33. The process as claimed in claim 2, wherein the cell is transformed with a recombinant vector comprising a nucleic acid molecule encoding the fusion protein.

34. The process as claimed in claim 32, wherein the recombinant vector has the nucleotide sequence of SEQ ID NO. 9.

35. The process as claimed in claim 33, wherein the recombinant vector has the nucleotide sequence of SEQ ID NO. 9.

36. A process for detecting the absence of γ-secretase in a cell in vitro, comprising:

a) transforming the cell with a nucleic acid encoding a fusion protein having (i) a first amino acid sequence comprising GAIIGLMVGGVVIATVIVITLVML (SEQ ID NO. 1); wherein said first amino acid sequence comprises a transmembrane domain; (ii) a signal peptide fused to the N-terminal end of the first amino acid sequence, and (iii) a protein located at the C-terminal end of the first amino acid sequence and containing a DNA-binding domain and a transcription-activating domain, wherein the fusion protein is expressed in the cell, and whereby if γ-secretase is present in the cell, the fusion protein is cleaved into a first partial protein containing amino acid sequence GAIIGLMVGGVV (SEQ ID NO. 2), and a second partial protein containing amino acid sequence VIVITLVML (SEQ ID NO. 3);

b) transforming the cell with a reporter gene under the control of a regulatable promoter, wherein protein of (iii) regulates the promoter; and c) detecting whether the reporter gene is expressed, thereby detecting whether the first partial protein or the second partial protein is present, whereby the absence of reporter gene expression indicates the absence of the first partial protein or the second partial protein, which indicates the absence of γ-secretase activity, and thus, the absence of γ-secretase in the cell.

37. The process as claimed in claim 1, wherein the cell is cotransfected with a cDNA bank.

38. The process as claimed in claim 37, where cDNA prepared from human or non-human tissue or human or non-human cells is present in the cDNA bank.

39. The process as claimed in claim 1, wherein the DNA-binding domain is a Gal4-binding domain and the transcription-activating domain is a VP16 transcription-activating domain (Gal4-VP 16).

* * * * *